(12) United States Patent
Bardwell et al.

(10) Patent No.: US 8,986,997 B2
(45) Date of Patent: Mar. 24, 2015

(54) METHODS AND COMPOSITIONS FOR INCREASING BIOLOGICAL MOLECULE STABILITY

(75) Inventors: James Bardwell, Ann Arbor, MI (US); Linda Foit, Ann Arbor, MI (US); Ajamaluddin Malik, Ann Arbor, MI (US); Tobias Baumann, Bad Zwesten (DE); Maximilian Kern, Attenkirchen (DE)

(73) Assignee: The Regents of the University of Michigan, Ann Arbor, MI (US)

( * ) Notice: Subject to any disclaimer, the term of this patent is extended or adjusted under 35 U.S.C. 154(b) by 1208 days.

(21) Appl. No.: 12/199,060

(22) Filed: Aug. 27, 2008

(65) Prior Publication Data

US 2009/0092982 A1 Apr. 9, 2009

Related U.S. Application Data

(60) Provisional application No. 60/969,177, filed on Aug. 31, 2007.

(51) Int. Cl.
| | |
|---|---|
| C12N 15/85 | (2006.01) |
| C12P 21/00 | (2006.01) |
| C12N 15/10 | (2006.01) |
| C07K 14/53 | (2006.01) |
| C12N 9/12 | (2006.01) |

(52) U.S. Cl.
CPC ............ *C12N 15/1079* (2013.01); *C07K 14/53* (2013.01); *C12N 9/12* (2013.01); *C12Y 207/01095* (2013.01)
USPC .......................... 435/455; 435/69.7; 435/70.1

(58) Field of Classification Search
None
See application file for complete search history.

(56) References Cited

U.S. PATENT DOCUMENTS

| | | | |
|---|---|---|---|
| 5,116,750 A | 5/1992 | Gelfand et al. | |
| 5,830,457 A | 11/1998 | Gicquel et al. | |
| 6,270,964 B1 | 8/2001 | Michnick et al. | |
| 6,428,951 B1 | 8/2002 | Michnick et al. | |
| 6,509,452 B1 | 1/2003 | Filho et al. | |
| 6,627,186 B1 | 9/2003 | Dahiyat et al. | |
| 6,709,861 B2 | 3/2004 | Mead et al. | |
| 6,897,017 B1 | 5/2005 | Michnick et al. | |
| 6,977,160 B2 * | 12/2005 | Yanagawa et al. | ............ 435/69.7 |
| 7,067,644 B2 | 6/2006 | Goryshin et al. | |
| 7,105,307 B2 | 9/2006 | Colyer et al. | |
| 2003/0108869 A1 | 6/2003 | Michnick et al. | |

FOREIGN PATENT DOCUMENTS

EP 1564286 A1 8/2005

OTHER PUBLICATIONS

Studier et al., "Use of T7 RNA Polymerase to Direct Expressions of Cloned Genes," Methods Enzymol. 185 (1990), pp. 60-89.
Braun et al, "High throughput protein production for functional proteomics," Trends Biotechnol. 21 (2003), pp. 383-388.
Peti et al, "Strategies to maximize heterologous protein expression in *Escherichia coli* with minimal cost," Protein Expression and purification, Jan. 2007, vol. 51 pp. 1-10.
Christendat et al, "Structural proteomics of an archaeon" Nat Struct Biol 7 (2000), pp. 903-909.
Makrides, "Strategies for achieving high-level expression of genes in *Escherichia coli*," Microbiol Rev 60 (1996), pp. 512-538.
Marsischky et al., "Many Paths to Many Clones: A Comparative Look at High-Throughput Cloning Methods," Genome Res 14 (2004), pp. 2020-2028.
Pearlberg, "Protein expression clone repositories for functional proteomics," Curr Opin Chem Biol 8 (2004), pp. 98-102.
Berthold et al, "Screening for functional expression and overexpression of a family of diiron-containing interfacial membrane proteins using the univector recombination system" Protein Sci 12 (2003), pp. 124-134.
Mirous et al, "Over-production of proteins in *Escherichia coli*: mutant hosts that allow synthesis of some membrane proteins and globular proteins at high levels," J. Mol. Biol. 260 (1996), pp. 289-298.
Brinkmann et al, "High-level expression of recombinant genes in *Escherichia coli* is dependent on the availability of the dnaY gene product," Gene 85 (1989), pp. 109-114.
Prinz et al, "The Role of the Thioredoxin and Glutaredoxin Pathways in Reducing Protein Disulfide Bonds in the *Escherichia coli* Cytoplasm," J. Biol. Chem. 272 (1997), pp. 15661-15667.
Hunt, "From gene to protein: a review of new and enabling technologies for multi-parallel protein expression," Protein Expr. Purif. 40 (2005), pp. 1-22.
Tao et al, "Milestones in directed enzyme evolution," Curr Opin Chem Biol 6 (2002), pp. 858-864.
Roodveldt et al, "Directed evolution of proteins for heterologous expression and stability," Current Opinion in Structural Biology, vol. (2005), pp. 50-56.
Waldo, "Genetic screens and directed evolution for protein solubility," Current Opinion in Chemical Biology, 2003, 7:33-38.
Kotz et al, "Phage-display as a tool for quantifying protein stability determinants," Eur J. Biochem, 2004, 271:1623.
Woolfson, "Core-directed protein design," Curr Opin Struct biol, 2001, 11:464.
Forrer et al, "Beyond binding: using phage display to select for structure, folding and enzymatic activity in proteins," Curr Opin Strut Biol, 1999, 9:514.
Barakat et al, "Exploiting elements of transcriptional machinery to enhance protein stability," J. Mol Biol, 2007, 366:103.
Vandevenne et al, "Rapid and easy development of versatile tools to study protein/ligand interactions," Protein Eng Des Sel. Jul. 2008;21(7):443-51.
Eglitis, "Positive selectable markers for use with mammalian cells in culture," Hum. Gene Ther. 1991 Fall;2(3):195-201.
Miki et al, "Selectable marker genes in transgenic plants: applications, alternatives and biosafety," J Biotechnol. 2004 107(3):193-232.
Michnick et al, "Detection of protein-protein interactions by protein fragment complementation strategies.," (2000), Methods in enzymology 328, 208-30.
Paschon et al, "Enhanced catalytic efficiency of aminoglycoside phosphotransferase (3')-IIa achieved through protein fragmentation and reassembly ," (2005) JMB, 353, 26-37.

(Continued)

*Primary Examiner* — Celine Qian
(74) *Attorney, Agent, or Firm* — Tanya A. Arenson; Casimir Jones, S.C.

(57) ABSTRACT

The present invention relates to methods and compositions for enhancing folding and stability of biological molecules. In particular, the present invention relates to methods and compositions for identifying biological molecules with enhanced stability. The present invention further relates to host cells that confer enhanced stability to biological molecules expressed therein.

18 Claims, 34 Drawing Sheets

(56) References Cited

OTHER PUBLICATIONS

Chautard et al, "An activity-independent selection system of thermostable protein variants," (2007) Nature Methods, 4 (11) 919-921.

Hu et al, "Development of a novel recombinant adenovirus containing gfp-zeocin fusion expression cassette for conditional replication in p53-deficient human tumor cells," J Virol Methods (2004) 117,129-136.

Delisa et al, "Folding quality control in the export of proteins by the bacterial twin-arginine translocation pathway," (2003) Proc Natl Acad Sci U S A. 100, 6115-6120.

Barany, "Single-stranded hexameric linkers: a system for in-phase insertion mutagenesis and protein engineering ," Gene. 1985;37(1-3):111-23.

Hallet et al, "Pentapeptide scanning mutagenesis: random insertion of a variable five amino acid cassette in a target protein," Nucleic Acids Res. May 1, 1997;25(9):1866-7.

Zebala et al,"Mapping catalytically important regions of an enzyme using two-codon insertion mutagenesis: a case study correlating beta-lactamase mutants with the three-dimensional structure," Gene. Apr. 1991;100:51-7.

Barany, "Two-Codon Insertion Mutagenesis of Plasmid Genes by Using Single-Stranded Hexameric Oligonucleotides," Proc Natl Acad Sci U S A. Jun. 1985;82(12):4202-6.

Park et al, "Energetics-based protein profiling on a proteomic scale: identification of proteins resistant to proteolysis," J Mol Biol. May 18, 2007;368(5):1426-37.

Parsell et al, "The structural stability of a protein is an important determinant of its proteolytic susceptibility in *Escherichia coli*," J Biol Chem. May 5, 1989;264(13):7590-5.

* cited by examiner

FIGURE 5
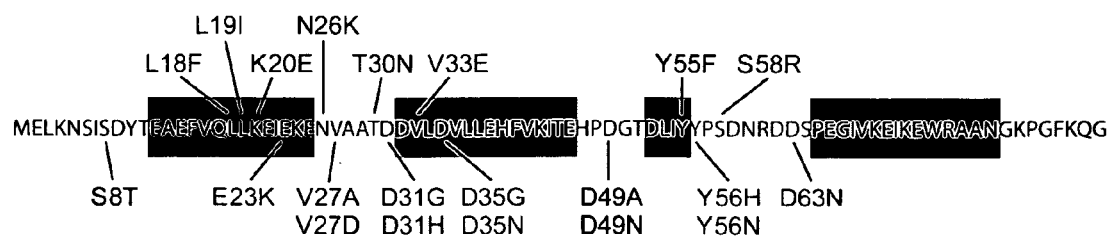
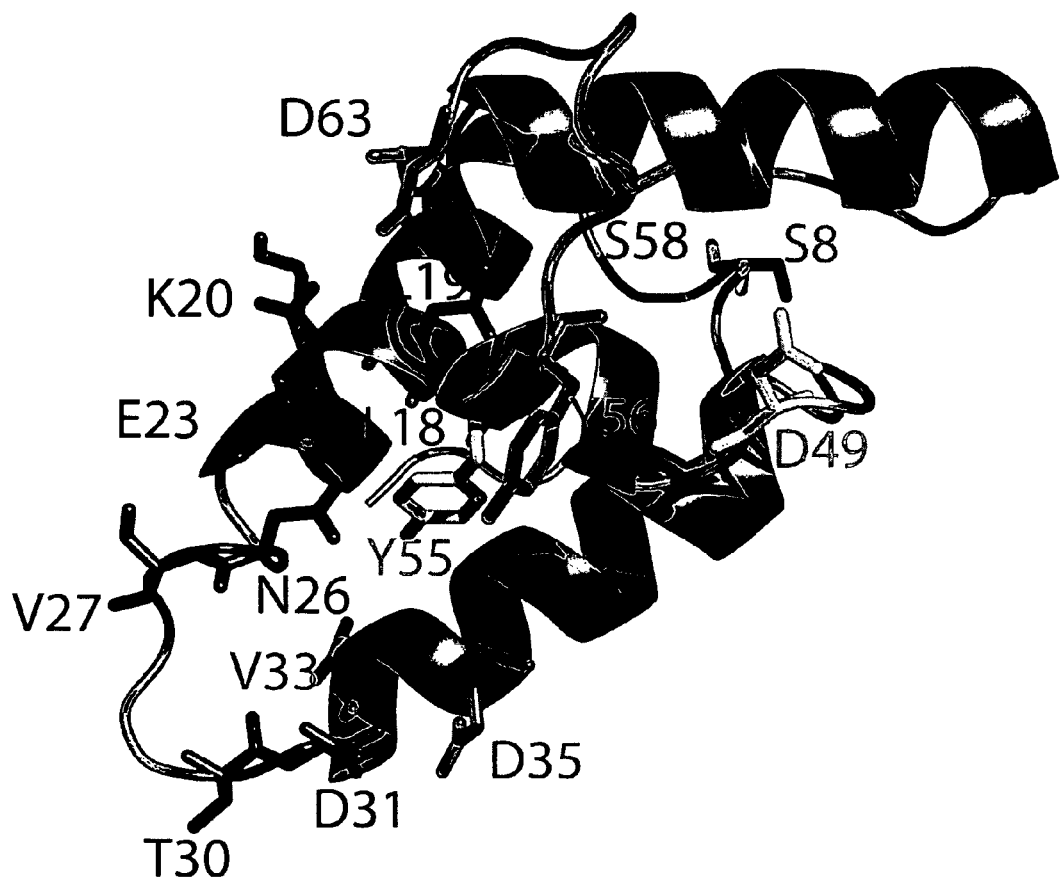

Figure 25

In 50 Im7 homologues:
➡ PSI-Blast search (1iteration) + Multiple Alignment with ClustalW

| Im7 Mutant | Frequency in Im7 homologues | ClustalW conservation index |
|---|---|---|
| S6T | 4.0% | 3 |
| L18F | 54.0% | 9 |
| L19I | 24.0% | 9 |
| E23K | 2.0% | 1 |
| N26K | 4.0% | 1 |
| V27D | 0.0% | - |
| V27A | 2.0% | - |
| T30N | 0.0% | 0 |
| D31G | 4.0% | 2 |
| D31H | 0.0% | 2 |
| V33E | 24.0% | 2 |
| D35N | 12.0% | 3 |
| D49A | 18.0% | 2 |
| Y56N | 2.0% | 6 |
| S58R | 6.0% | 2 |
| D63N | 2.0% | 9 |

Figure 27

```
aph2*1a    M.E....YRYDDNATNVKAMKYLIEHYPDNPKVDSIEIIGS .YDSVA LV......NNEYIP .TKFST
aph2*1b    M......VNLDAEI.........YBH NKQIKINELRYLSS .DD    C......NEQYVV VPKRDS
aph2*1c    MKQ....NKLHYTT.........MIMTQPPDISIQSVESLGE .FR V36 V...NGDWVFR P SQQ
aph2*1d    MRT....YTFDQVE...KA....IEQ YPDFTINTIEISGE .ND    I......NRKFI FPKHSR
aph3'i     MSHIQRETSCSRPR........LNSNMDADLYGYKWARDNV Q GAT RLYGKP.DAPEL HGKGSV
aph3'iia   MIE...QD.GLHAG........SPAAWVERLFGYDWAQQTI CSDAA PRLSA.Q.GRPVL VKTDLSGA   56
aph3'iib   MHD...AATSMPPQ........APSTWADYLA XRWRGQGE C AAT HRLEA   RRPTL V QEV A
aph3'iii   MAK.......MR..........ISPE KKL    CVKDTE MSPAK KLV     NENL LKMT          50
aph3'iv    MNE.......STRN........WPBE LEL  21 LTVNKI Y GDH HVK 42 GTPA L IA  55
aph3'v     MDD...................ST RRK    WHAVNE D GAF QLT    QPBLYA IA
aph3'vi    ............ME........LPNIIQQFIGNSVLEPNKI Q PSD SFNR...NNETF RSSTLY
aph3'vii   ............MK........YIDEIQILG...KC...SE M PAE KCQL...KNTVCYL KIDDIF
aph3'viii  MNDIDREEPCAAAA........VPBSMAAHVMGYKWARDKV Q GCA RLHSKS.GGSDL HGKDAF
rib-ph     ME....................ST RRTYPHHTWHLVNE D GAP RLTG...HGPELYA IAPRTP
aph3'-Dr   MMS...DASLPALT........LPPA RRVLPAARWERVTE E GAG WR....S.TRFVVKV QSRTLYP
str3*kin   MSD...HPGPGA..........VTPE FGV.G.GDWLAVTA E GAS FRA....ADATRYA CVPAAD
aph-Tb     MSP.....PSSPPA........LPAIVARPAVGRPVRAVWVN ELGGVT RVDS.GMGAGCE I VARRGT
kank-Ec    MSEWRRQQVCAPIP........MPASMATSLEGYQWAPITI E GSN RLYGKP.KAPDL RGKYDV
                                              xG-xGxxGx(I)       xxEx(II)

- conserved      - ATP-binding aph2*1a    NKK..KGYAK KAIYNF NT.N ETNVKI NIEYSYISDE...LSILGYKE K TFLTPEIYSTMS EEQ
aph2*1b    VRI..SQK.R F LYRP ENCK S..YQI AV VQ..SDR...PNIMKY.. K BRITYEQYHKLS KEK
aph2*1c    GAD..ELN.K IEL PL VGC.VK..VNI QY YIGKRS G..NPFVGYRKVQ QILGEDGMAVPPDDAK
aph2*1d    GST..NLP.N VNI KRIHN.K P..LPI EV PTGMPSETYQMSPAGFTK KGVPLTPLLLNNLPKQSQ
aph3'i     AN...DVT.D MVR NW TEF.MP....L T.IKHFIRTPD..DAK LTTA PGKTAFQVLEEYPDS..G
aph3'iia   LN...ELQ.D AAR SW ATTGVP....CAA.VLDVVTBAG..RDW LLG EVPG QDL.LSSH..LA..E  109
aph3'iib   HA..   P.A IAR R LHGAGID...CE Q.VLNETQSDG..RQW LMS MP DTLSALAQRDEL ..P
aph3'iii   KGT.    .R KDMML EGK. P...VE K.VLHFERHDG..WSN LM EAD VLC...SSEYBD QSP  108
aph3'iv    WR.. 59 .P IEA A LDGK. P....VE K.ILYTAEHGG..MDY LMB LG KDGS..HETIQAK..R
aph3'v     ENSA  G.A DR E HRHGIP...VE R.VVERGAD T..AAW VTE VPG VAAA..EEWPEHQ..R
aph3'vi    TETTYSVS.R AKM S SEK. K....VE ELIMTFQ.DEQ..FEFMITKA NAKPI...SALFLTD...
aph3'vii   SKTTYSVK.R AEMMM SDK. K....VED.VIEYGVREH..SEY IMSELR KH....IDCFIDH..P
aph3'viii  AD...EVT.D MVR R AGH.IS...VE S.VVSFVRTPN..QAW LTTA HGKTAYQVLKSDFGA..R
rib-ph     ENSAFHLD.G AD R D ARHGIS...VE R.VVERGAD T..TAW VTE VPG AAAS..EEWPED ..R
aph3'-Dr   AS...TLL.Q RER R NFAGR. P...VE Q.VVAYEDDGE..QEY AMTRL P IAMS..HPDAALH..P
str3*kin   AA...GLE.A RDR A I SGQGVP....G R.VLDWYAG A..GAC VTR VPG VPA..DRVGADD..L
aph-Tb     A....EFA.N AR R R AAPY. A....VE R.VLGVGVDGD..WAW HTD LP LSA..VHPRWRAS..D
kank-Ec    AD... VT.D MVR R AER.IP....V T.VVNFVRTLD..EAW LTTA MP GRTVYEELEANPDA..C
                       xEx(III)                              Nurizzo et al., 2003
```

METHODS AND COMPOSITIONS FOR INCREASING BIOLOGICAL MOLECULE STABILITY

This application claims priority to provisional patent application Ser. No. 60/969,177, filed Aug. 31, 2007, which is herein incorporated by reference in its entirety.

This invention was made with government support under GM057039 and GM064662 awarded by the National Institutes of Health. The government has certain rights in the invention.

FIELD OF THE INVENTION

The present invention relates to methods and compositions for enhancing folding and stability of biological molecules. In particular, the present invention relates to methods and compositions for identifying biological molecules with enhanced stability and expression. The present invention further relates to host cells that confer enhanced stability to biological molecules expressed therein.

BACKGROUND OF THE INVENTION

Expressing high levels of stable and functional proteins remains the bottleneck of many scientific and biotechnological endeavors including the determination of protein structures and producing proteins for therapeutic purposes (Roodveldt et al., Current Opinion in Structural Biology, 15:50 (2005)). Large amounts of protein, usually between 5 and 50 mg, are required for every structural biology project (Edwards et al., Nat. Struct. Biol. 7:970 (2000)). Even greater amounts of protein and peptides are required for industrial, and pharmaceutical purposes. The inability to express proteins effectively in bacteria often leads to very high costs for pharmaceutical proteins and peptides. The cost of recombinant insulin in the US, for instance, is $3.3 billion dollars a year. granulocyte-colony stimulating factor (or G-CSF), which, under the trademark names of Neopogen and Neulasta, is used to treat cancer and AIDS patients. The wild type protein has a high tendency to aggregate, and needs to be stored under special conditions. The stability problems associated with the wild type G-CSF protein contributes to its phenomenal retail price of $500,000-$1,170,000/gm. Despite its high cost, G-CSF is effective, and $4.28 billion dollars of this drug were sold in 2007 (Amgen annual report 2007). The total global market for protein drugs was $47.4 billion in 2006.

*Escherichia coli* is the preferred host for recombinant protein expression for structural studies and pharmaceutical purposes because it is rather easy to genetically manipulate, it is relatively inexpensive to culture, labeling protocols for structural studies are established, and expression is fast (Studier et al., Methods Enzymol. 185 (1990), pp. 60-89; Braun and LaBaer, Trends Biotechnol. 21 (2003), pp. 383-388; Peti and Page, Protein Expression and purification Volume 51 pages 1-10. January, 2007). There are a wide variety of commercial products available for the *E. coli* expression system. However, there are disadvantages to using *E. coli* as an expression host. Many proteins fail to express in *E. coli*, or express, but do so as insoluble inclusion bodies. Data from one bacterial species indicates that at least 50% of non-membrane genes will require further optimization to obtain soluble or stable proteins for crystallization (Christendat et al., Nat Struct Biol 7 (2000), pp. 903-909).

During the last few years, both the pharmaceutical industry and the structural genomics community have made significant efforts to develop methods to overcome these problems. Conventional approaches to the production of soluble and active proteins in heterologous expression systems include low-temperature expression, promoters with different strengths, modified growth media and a variety of solubility-enhancing fusion tags (reviewed in Makrides, Microbiol Rev 60 (1996), pp. 512-538; Braun and LaBaer, Trends Biotechnol 21 (2003), pp. 383-388; Marsischky and LaBaer, Genome Res 14 (2004), pp. 2020-2028; Pearlberg and LaBaer, Curr Opin Chem Biol 8 (2004), pp. 98-102). A series of vectors and fusion partners that can be screened for high-level functional expression of a target protein have been developed (Berthold et al., Protein Sci 12 (2003), pp. 124-134). In addition, a few *E. coli* strains that facilitate the expression of membrane proteins (Miroux and Walker, J. Mol. Biol. 260 (1996), pp. 289-298), proteins with rare codons (Brinkmann et al., Gene 85 (1989), pp. 109-114), proteins with disulfide bonds (Prinz et al., J. Biol. Chem. 272 (1997), pp. 15661-15667), and proteins that are otherwise toxic to the cell have been developed. This variety of expression vectors and cell lines now significantly enhances the likelihood of designing an *E. coli* protein expression protocol suitable for the production of the substantial amounts of protein required for structural studies (Hunt, Protein Expr. Purif 40 (2005), pp. 1-22). However, there are still many challenges to getting a protein to express in a suitable format.

In the past several years, directed evolution has emerged as an alternative approach to rational design, enabling the improvement of structural and functional properties, such as stability and performance under different conditions (e.g., at extreme temperatures and pH, and in organic co-solvents), or changes in their reaction and substrate specificity (Tao and Cornish, Curr Opin Chem Biol 6 (2002), pp. 858-864). Rather than designing a limited number of site-directed mutants, directed evolution implements an iterative Darwinian optimization process, whereby the fittest variants are selected from an ensemble of random mutations. Improved variants are identified by screening or selection for the properties of interest and their encoding genes are then used as parent genes for the following round of evolution (Roodveldt et al., supra). Individually testing all the available variants in expression constructs and available bacterial strains often helps and robotics has assisted in this matter significantly.

Computational methods have also been used to predict protein stability. One method used to predict mutations with higher stability is the proprietary "protein design automation methodology that is the subject of U.S. Pat. No. 6,627,186.

However; a new approach is clearly needed.

SUMMARY OF THE INVENTION

The present invention relates to methods and compositions for enhancing folding and stability of biological molecules. In particular, the present invention relates to methods and compositions for identifying biological molecules with enhanced stability and expression. The present invention further relates to host cells that confer enhanced stability to biological molecules expressed therein.

In some embodiments, the present invention provides a method, comprising: introducing one or more expression constructs encoding a multipartite fusion molecule (e.g., a tripartite or greater fusion molecule), wherein the expression constructs comprises a first gene encoding a molecule of interest inserted into or associated with a second gene that encodes a screenable (e.g., selectable) phenotype, into a plurality of host cells; and culturing the host cells under conditions such that fusion molecules comprising an functional selectable or screenable marker gene are selected or screened for. In some embodiments, the selectable or screenable marker gene encodes DHFR (dihydrofolate reductase), β-lactamase, aminoglycoside phosphotransferase (3')-IIa, ShBle, green fluorescent protein (GFP) and various yellow, blue and red fluorescent proteins (YFP, CFP and RFP), Renilla and firefly luciferase, GAR transformylase, or aminoglycoside hygrotransferase, however, the gene for any suitable screenable (e.g., selectable) marker may be used. In some embodiments, the gene of interest encodes a pharmaceutical protein (e.g., protein fragment, enzyme, peptide, antibody, etc.), an industrial protein, a research protein, an RNA molecule, and the like. In some embodiments, optimized (e.g., stabilized) proteins of interest are used in research, drug screening, industrial or therapeutic applications. However, the invention is not limited by the nature of the gene of interest. In some embodiments, the one or more expression constructs encode a series of variants of the molecule of interest. In some embodiments, the variants comprise amino acid changes. In some embodiments, the variants result in altered disulfide bond formation, altered hydrophobic interactions, or altered salt bridges in the molecule of interest. In some embodiments, culturing the host cell comprises contacting the host cell to a range of antibiotic concentrations or other stressors that challenge the screenable marker. In some embodiments, cells containing fusion molecules that grow at the highest concentrations of antibiotics comprise the most stable molecule of interest. In some embodiments, the gene of interest is inserted into a location in the second gene that retain the ability of the product encoded by the second gene to maintain at least a portion of its screenable phenotype (e.g., in between amino acids 196 and 197 of β-lactamase). The present invention is not limited by the nature of the host cell used. In some embodiments, the host cell is a bacterial cell (e.g., E. coli), eukaryotic cell or archaeal cell. In some embodiments, the host cell chromosome has one or more variant genes that optimize the ability of the cell to express a stable molecule of interest, either generally or for a specific molecule of interest. In some embodiments, the method is a selection method. In some embodiments, the method is a high throughput screening method.

In some embodiments, the present invention further provides kits, systems, and compositions (e.g., reaction mixtures, sets of reagents, host cells, etc.) comprising one or more components necessary for, sufficient for, or useful for carrying out the methods. For example, in some embodiments, kits, systems, or compositions comprise expression constructs described above, instructions for use, software, host cells, antibiotics, control samples (e.g., positive and negative control samples, including host cells or expression vectors having stable and unstable molecules of interest therein), culture media, multi-well plates or other reaction vessels, and the like. In some embodiments, the kits, systems, and composition comprise reagents or other components useful in generating variations in genes, proteins, or host cells.

In further embodiments, the present invention provides expression vectors comprising the constructs described above and host cells comprising the constructs. For example, in some embodiments a collection of expression vectors is provided, the collection containing a first vector housing a gene encoding a molecule of interest inserted into a gene encoding a selectable or screenable marker and a second vector housing a gene encoding a variant of the molecule of interest that is more or less well expressed than the molecule of interest inserted into the same selectable or screenable marker. Populations of vectors may comprise numerous (e.g., thousands, millions etc.) of variants of the molecule of interest to permit broad selection or screening of molecules having improved folding or stability properties. Host cells containing the vectors are also provided.

In yet other embodiments, the present invention provides host cells selected or optimized for expression of the expression constructs of the invention.

DESCRIPTION OF THE FIGURES

FIG. 5 shows mutants of Im7 chosen generated by random mutagenesis.

FIG. 25 shows the frequency of Im7 mutants in Im7 homologues.

FIG. 27 shows a sequence alignment of APH proteins.

DEFINITIONS

Figure 1:
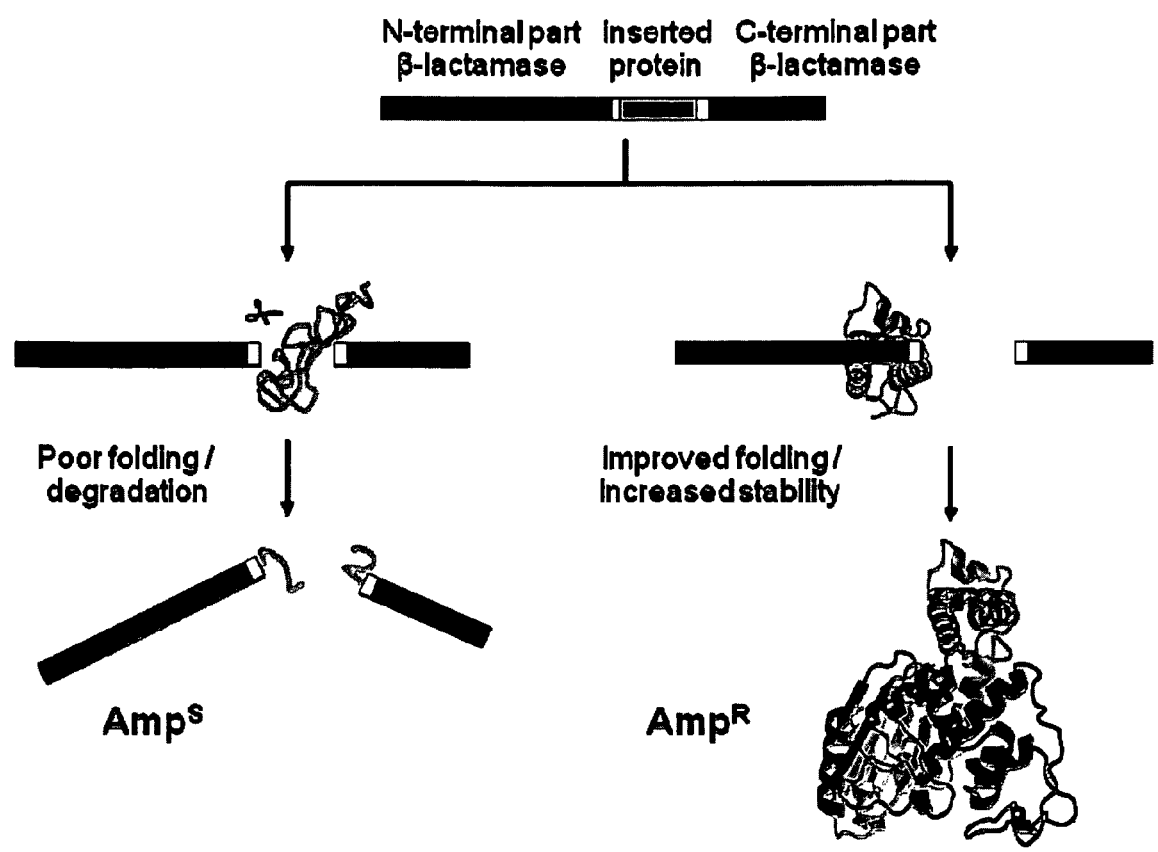
FIG. 1 provides an overview of the experimental methods used in embodiments of the present invention.

To facilitate an understanding of the present invention, a number of terms and phrases are defined below:

As used herein, the term "host cell" refers to any cell (e.g., bacterial, mammalian cells, avian cells, amphibian cells, plant cells, fish cells, eukaryotic cells, archaeal cells and insect cells) that can express a heterologous expression system. In some preferred embodiments of the present invention the host cell is *E. coli*.

As used herein, the term "vector" refers to any genetic element, such as a plasmid, phage, transposon, cosmid, chromosome, virus, virion, etc., which is capable of replication when associated with the proper control elements within an appropriate host cell. Thus, the term includes cloning and expression vehicles, as well as viral vectors.

The term "nucleotide sequence of interest" refers to any nucleotide sequence (e.g., RNA or DNA), the manipulation of which may be deemed desirable for any reason (e.g., treat disease, confer improved qualities, expression of a protein of interest in a host cell, expression of a ribozyme, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

As used herein, the term "molecule of interest" refers to a molecule (e.g., protein, or RNA) encoded by a nucleic acid of interest.

As used herein, the term "protein of interest" refers to a protein encoded by a nucleic acid of interest.

As used herein, the term "pharmaceutical protein" refers to a protein that is administered to a subject to treat, prevent or reduce the symptoms of a medical condition or disease or to improve or maintain the health of a subject.

As used herein, the term "industrial protein" refers to a protein that is not administered to a subject. In some embodiments, industrial protein are enzymes. Industrial proteins are typically used in food feed, detergents, textiles, leather, and pulp & paper and the like.

As used herein, the term "exogenous gene" refers to a gene that is not naturally present in a host organism or cell, or is artificially introduced into a host organism or cell.

The terms "specific binding" or "specifically binding" when used in reference to the interaction of two binding partners means that the interaction is dependent upon the presence of a particular structure (e.g., region) on the proteins; in other words the binding partners are recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an two binding partners refer to an interaction that is not dependent on the presence of a particular structure (e.g., the protein is binding to proteins in general rather that a particular structure such as an epitope).

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N6-methyladenosine, aziridinylcytosine, pseudoisocytosine, 5 (carboxyhydroxyl-methyl) uracil, 5-fluorouracil, 5 bromouracil, 5-carboxymethylaminomethyl 2 thiouracil, 5 carboxymethyl-aminomethyluracil, dihydrouracil, inosine, N6 isopentenyladenine, 1 methyladenine, 1-methylpseudouracil, 1 methylguanine, 1 methylinosine, 2,2-dimethyl-guanine, 2 methyladenine, 2 methylguanine, 3-methylcytosine, 5 methylcytosine, N6 methyladenine, 7 methylguanine, 5 methylaminomethyluracil, 5-methoxy-amino-methyl 2 thiouracil, beta D mannosylqueosine, 5' methoxycarbonylmethyluracil, 5 methoxyuracil, 2 methylthio N6 isopentenyladenine, uracil 5 oxyacetic acid methylester, uracil 5 oxyacetic acid, oxybutoxosine, pseudouracil, queosine, 2 thiocytosine, 5-methyl-2 thiouracil, 2-thiouracil, 4 thiouracil, 5-methyluracil, N-uracil 5 oxyacetic acid methylester, uracil 5 oxyacetic acid, pseudouracil, queosine, 2-thiocytosine, and 2,6 diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g., mRNA, rRNA, tRNA, siRNA, miRNA, or snRNA) through "transcription" of the gene (e.g., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule increase the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA or protein to indicate a level of expression approximately 2-fold higher (or greater) than that observed in a given tissue in a control. Levels of mRNA or protein are measured using any of a number of techniques known to those skilled in the art. Techniques for measuring overexpression of mRNA include, but are not limited to, Northern blot analysis and quantitative immunofluorescence. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA. Protein levels can be estimated by a number of means, including but not limited to, performing a Western blot against the protein of interest, whereby cellular lysate is separated on a polyacrylamide gel and then probed with an antibody to the protein of interest. The antibody can either be conjugated to a fluorophore or to horseradish peroxidase for imaging or quantification. Another commonly used method for assaying the amount of a particular protein in a cell is to fuse a copy of the protein to a reporter gene such as Green fluorescent protein, which can be directly imaged using a fluorescent microscope.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

As used herein, the term "screenable marker", refers to any marker that allows one to distinguish (e.g., screen) groups of cells into categories. In some embodiments, screenable markers allow one to distinguish between cells comprising stabilized and un-stabilized genes or interest. In some embodiments, screenable markers provide a protein that can be identified through various laboratory assessments (e.g., screening tools such as growth conditions, visual inspection or the like). In some embodiments, screenable markers are "selectable markers."

As used herein, the term "selectable marker" refers to markers that can be selected for using growth or assay conditions. In some embodiments, selectable markers provide an enzymatic activity that confers the ability of an organism to grow on or in a medium at a faster rate than similar organisms that lack the selectable marker. In some embodiments, a selectable marker is provided by a gene introduced into a cell (e.g., a bacterium or other cells in culture), which confers a trait suitable for artificial selection. In some embodiments, selectable markers are provided by antibiotic resistance genes; organisms that contain the antibiotic resistance gene can grow on media that contain this antibiotic, whereas those that do not contain the antibiotic resistance gene cannot or grow more poorly. Some markers can be used as both selectable markers and sceenable markers. GFP, for example, can be visually identified by its green fluorescence. GFP used in conjunction with a fluorescence-activated cell sorter (FACS) functions as a selectable marker.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "prokaryotes" refers to a group of organisms that usually lack a cell nucleus or any other membrane-bound organelles. In some embodiments, prokaryotes are bacteria. The term "prokaryote" includes both archaea and eubacteria.

As used herein, the term "in vitro" refers to an artificial environment and to processes or reactions that occur within an artificial environment. In vitro environments can consist of, but are not limited to, test tubes, microtiter plates, and the like. The term "in vivo" refers to the natural environment (e.g., an animal or a cell) and to processes or reactions that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

As used herein, the term stability refers to measures of the ability of a molecule (e.g., protein) to resist unfolding by various treatments (e.g., including but not limited to, increased temperature, presence of chemicals such as denaturants including urea or guanidinium, or detergents such as sodium doecyl sulfate). Stability also refers to the ability of the molecule to resist degradation by enzymes or compounds that can act to cleave the molecule including but not limited to, resistance of proteins to proteolytic enzymes. Stability can refer to either or thermodynamic stability (e.g., extent of unfolding) or kinetic stability (e.g., rate of unfolding).

DETAILED DESCRIPTION OF THE INVENTION

The present invention relates to methods and compositions for enhancing folding, expression and stability of biological molecules. In particular, the present invention relates to methods and compositions for identifying biological molecules with enhanced stability. The present invention further relates to host cells that confer enhanced stability to biological molecules expressed therein.

Methods to direct the evolution of protein stability have recently been reviewed (Roodveldt et al., Current Opinion in Structural Biology, Volume (2005), Pages 50-56). Screening or selecting for heterologous protein expression can be done in two ways: screening or selecting for the protein's own function or screening or selecting for the activity of a reporter protein. The disadvantage of screening or selecting for the proteins own function is that a different assay method needs to be developed for each protein. The method described herein eliminates this need by coupling the folding status and/or stability of the protein (or variant of a protein) to a screenable (e.g., selectable) phenotype imparted by a separate entity (e.g., antibiotic resistance). This screenable phenotype is used to assess stability. Screens where only the desired colonies grow are, in general, preferable to screens where the specific properties of each individual organism or bacterial colony needs to be determined. The latter procedure is often a very laborious and costly process that requires sophisticated and expensive equipment. Selections, where only the desired variants grow and all or nearly all of the undesirable variants fail to grow, are in general much better, because they allow one to examine a much larger number of potential variants. In addition, whereas screening procedures are performed on individual genes or clones that have to be organized/separated on microtiter plates, arrays, chips, agar plates, selection procedures have the advantage of being able to simultaneously act on the entire pool of mutated genes.

This allows one to do extensive mutagenesis. A variety of generic 'C-fusion' approaches have been developed that rely on expression of the target protein as an N-terminal fusion to a reporter protein with a screenable function. An insoluble target protein leads to the aggregation of the reporter protein and loss of its function. As an example, colonies overexpressing green fluorescent protein (GFP) fused to a soluble protein can be easily distinguished owing to GFP folding and fluorophore formation; colonies expressing an insoluble protein should not fluoresce (Roodveldt et al, supra). However, this is generally a screen, not a selection and many insoluble proteins do actually fluoresce when fused to GFP. This and other limitations, including the need for expensive cell sorting machines for this technique to work effectively. In addition, studies have only looked at the correlation between GFP fluorescence and solubility, not at a direct correlation between fluorescence of GFP and stability (See e.g., Waldo, 2003, Current Opinion in Chemical Biology, 7:33-38).

Four types of selections have been proposed to be useful for increased solubility or activity of proteins, CAT selection, thermophilic kan selection and LacZ alpha complementation and the PROSIDE technique. The CAT selection relies on chloramphenicol acetyltransferase (CAT) fusion, whereby selection for solubility of the target protein is performed by using antibiotic resistance to chloramphenicol. If the protein fused to CAT is insoluble it should drive CAT into insoluble inclusion bodies decreasing the chloramphenicol resistance of the bacteria carrying the fusion. This methodology was used as a preselection in conjunction with a subsequent screen for active enzyme variants in the conversion of insoluble human P450 cytochrome into a fairly soluble active protein. Unlike the methods described herein, the CAT fusion technique requires the heterologous protein to be very insoluble, if the heterologous protein is unstable, it will simply be cleaved away from the CAT portion of the fusion, leaving the CAT portion of the fusion to function normally. It remains to be seen whether the CAT fusion method is applicable to the wide range of targets encountered in structural genomics, because the CAT protein is an obligate trimer, and may lead to the formation of higher-order aggregates of otherwise soluble multimeric proteins. A similar problem has been encountered using tetrameric red fluorescent protein as a genetic marker of multimeric proteins (Waldo, 2003, Current Opinion in Chemical Biology, 7:33-38). In the thermophilic kanamycin selection system, a thermostable variant of kanamycin nucleotidyl transferase is used in *Thermus thermophilus* (FR2886943). In this selection system, proteins of interest are fused to the N-terminus of kanamycin nucleotidyl transferase. There are a number of general problems with N or C terminal fusions. There is no assurance that the presence of the test protein will affect the activity or solubility of the assayable fusion partner, and any mutation that simply removes the test protein should result in full activity of the assayable partner. This is reflected in the observation that frameshift and stop codons were among the clones selected with this thermophilic methodology. The presence of wild type fusion constructs that survived this selection and the very low concentrations of antibiotic used in this selection indicates that the method has a low selectivity. There are also a lot of difficulties of working with the hard to culture *T. thermophilus*, for example in terms of cultivation and transformation efficiency, compared to the model genetic organism and expression host, *E. coli*.

In the β-galactosidase complementation assay, a small, approximately 50 amino acid α-fragment is fused to the C terminus of the target protein, restoring—in those cases in which the target protein remains soluble—the β-galactosidase activity of a truncated lacZ form (lacZ-Ω) by complementation in trans. This was proposed as a selection, but the amount of active β-galactosidase produced by alpha complementation is insufficient for this technique to work as a selection. Because the C-fusion techniques do not depend on the function of the target protein, they are generally applicable and particularly advantageous when attempting to evolve new folds or when the target protein has no assigned function. Other potentially generic methodologies are based on screening by cellular stress responses to misfolded proteins, 'proteolytic selection' by phage display or 'protein stability increased by directed evolution' (Proside); the last two technologies are based on the principle that infectivity of the phage is coupled to protease resistance of the protein variants. This assumption in turn relies on the observation that proteolysis resistance can be used as a marker of foldedness.

The techniques and approaches described above are rather of qualitative than of quantitative nature and focus a general improvement of solubility, rather than a quantitative measure of stability.

A number of phage display techniques to monitor the stability of proteins have been used (reviewed by kotz et al Eur J. Biochem 271:1623, Woolfson Curr Opin Struct biol 11:464 and Forrer et al Curr Opin Strut Biol 9:514). Phage display methodologies are generally limited to small proteins or peptides and most involve bipartite fusions between the tested protein and the phage protein.

The PROSIDE technique involves a tripartite fusion, but in this case the protein to be destabilized is inserted into the Gene 3 protein of the phage fd. The activity of the phage fd protein is required for phage growth. Mutants in the inserted protein that stabilize its fold increase the ability of the phage to resist increasing levels of proteases and denaturants in vitro. The PROSIDE system uses the Gene 3 protein which is required for fd phage growth. Since the activity of the gene 3 protein is essential for the growth of the phage the PROSIDE technique is limited to selecting for increased stability of proteins that are already well folded. In embodiments of the present invention, antibiotic resistance, such as β lactam resistance, may be used and is not essential for the maintenance of the vector, which can carry other antibiotic resistance markers. Thus the methods of embodiments of the present invention allow for one to start with poorly folded proteins and increase their ability to fold.

Furthermore, in the PROSIDE technique the selections are done in vitro, in contrast to methods of embodiments of the present invention, which can be carried out in vivo. Proteins selected for protease resistance in vitro are not necessarily resistant to the numerous proteases present in vivo and thus may not express well in the cell.

Other advantages of the methods described herein include, but are not limited to, the ability to select for mutations in the host cell that are specifically or generally better at folding recombinant proteins and the general applicability to a variety of proteins.

Protein complementation (PCA) is used to look at protein-protein interactions. A reporter protein—for example, a monomeric enzyme or a fluorescent protein is engineered into fragments using rational design or alternative engineering methods. Although fragmentation would destroy the activity of the protein, if the complementary fragments were separately attached to other molecules that interact, the interaction of those other molecules would bring the complementary fragments into close proximity. The association of the fragments would enable the fragments to fold into an active tertiary structure, recapitulating the uni-molecular folding reaction and thereby reconstituting the activity of the original protein. The PCA principle has been applied to a variety of protein reporters including DHFR (dihydrofolate reductase), β-lactamase, green fluorescent protein (GFP) and various yellow, blue and red fluorescent proteins (See e.g., U.S. Pat. Nos. 6,270,964, 6,897,017, and US2003/0108869 (each of which is herein incorporated by reference)). However, these methods are used to look for interactions between different molecules, rather than to look for stability of a molecule.

A tripartite fusion that links the stability of the inserted protein to a transcriptional readout that controls antibiotic resistance has been developed (Barakat et al J. Mol Biol 366:103) where more stable proteins are less resistant to the antibiotic carbenicillin. Thus this methodology cannot be used as a selection for more stable variants though it can be used as a screen.

Beta-lactamase has been used as a carrier for the expression of heterologous proteins as part of a tripartite fusion setup (Vandevenne et al., 2008, Protein Eng Des Sel. 2008 July; 21(7):443-51). Whereas this approach was used to produce larger amounts of soluble proteins by cleaving the protein of interest from the carrier protein after purification of the hybrid, it was not used as an in vivo readout for the folding and stability status of the inserted guest protein.

There are also a variety of computational methods that can be used to predict the stability of proteins. Rational attempts to predict protein stability regularly require the existence of large experimental data within a group of structural homologs that can be used as a basic for the prediction. They very often rely on high resolution structures of the protein of interest, which are usually not available for a hard to express protein. Some of the prediction programs have been successfully used for certain proteins, but the chance of success is not easy to predict. This unpredictability may result from the observation that single amino acid substitutions have not only local effects on their close by neighbors, but can actually transfer conformational changes over larger distances, even in small proteins. Furthermore, none of the commonly available programs can take complex factors like induced charges, multiple protonation states, multibody interactions and multipole interactions into account.

Figure 31:
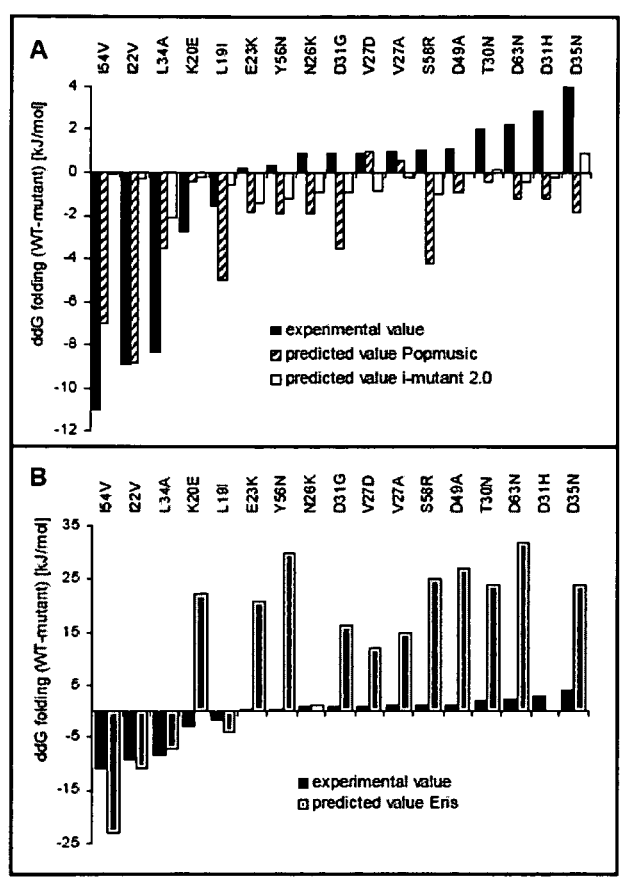
FIG. 31 shows a comparison between the actual stabilities of the Im7 mutants and the stabilities as predicted by 3 computational methods.

Experiments conducted during the course of development of embodiments of the present invention directly tested the ability of three of these programs PoPMuSiC, eris and i-mutant 2.0 to predict the stability of Im7 mutants (See experimental section below). As shown in FIG. 31 all of these programs did very poorly. I-mutant2.0 was the worst, giving no correspondence between the actual and predicted stabilities. For the stabilizing single amino acid substitutions mutations isolated, PoPMuSiC incorrectly predicted that 10/12 of them should be destabilizing. It performed significantly better with the previously isolated destabilizing mutations, correctly predicting that they should be destabilizing, although the value of the predicted change was accurate in only one case (I22V). One possible reason for this superior ability to predict destabilizing effect of mutants may be the fact that destabilizing mutants are much more common, which is reflected in the strong bias training set used to develop popmusic.

Figure 4:
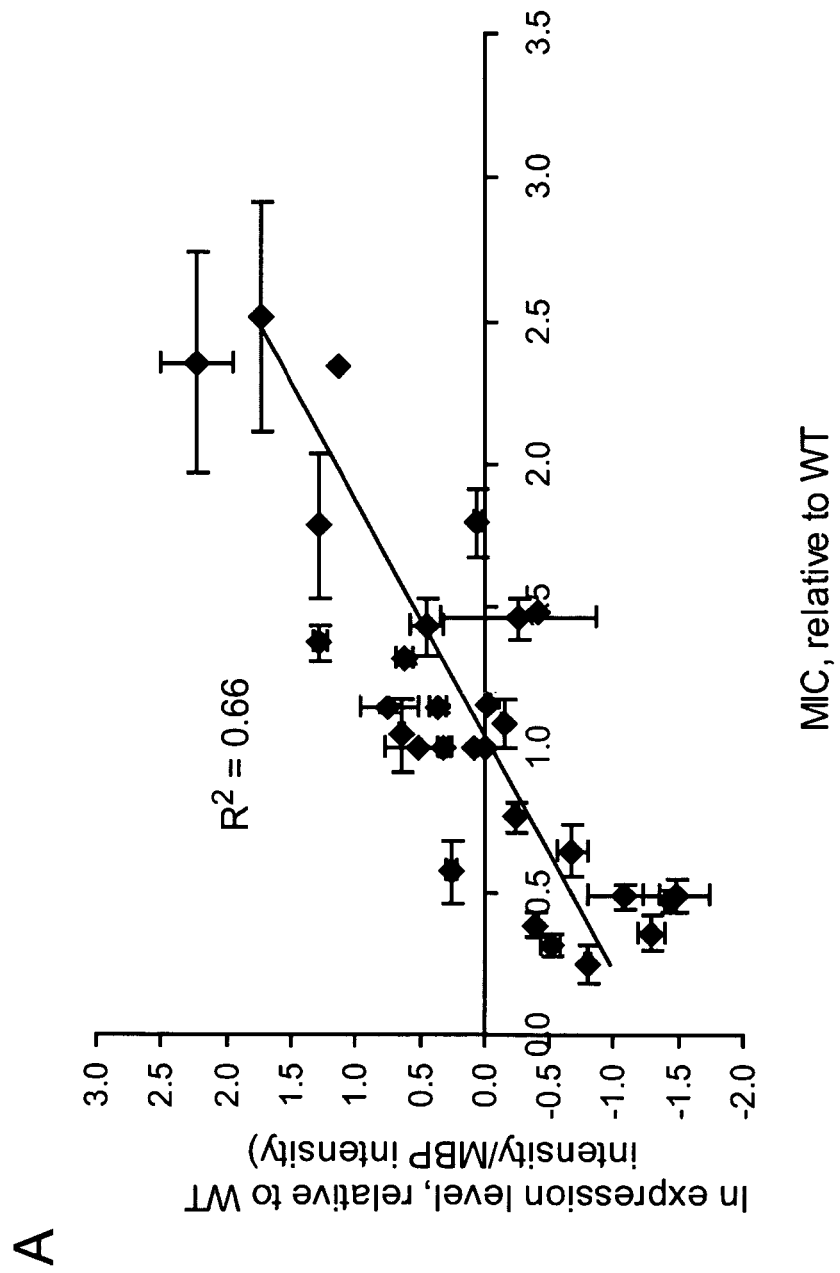
FIG. 4 shows expression levels of β-lactamase fusion proteins detected by Western blotting using a beta-lactamse antibody.
Figure 4:
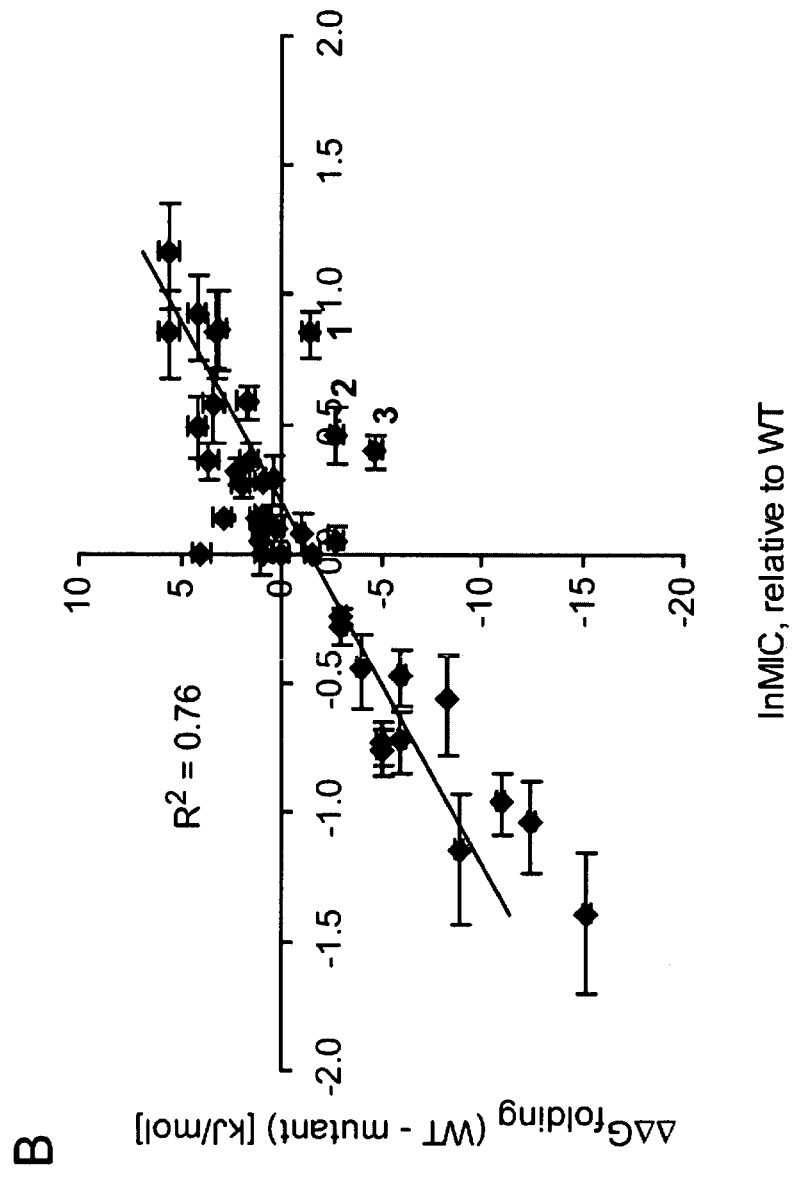
Figure 4:
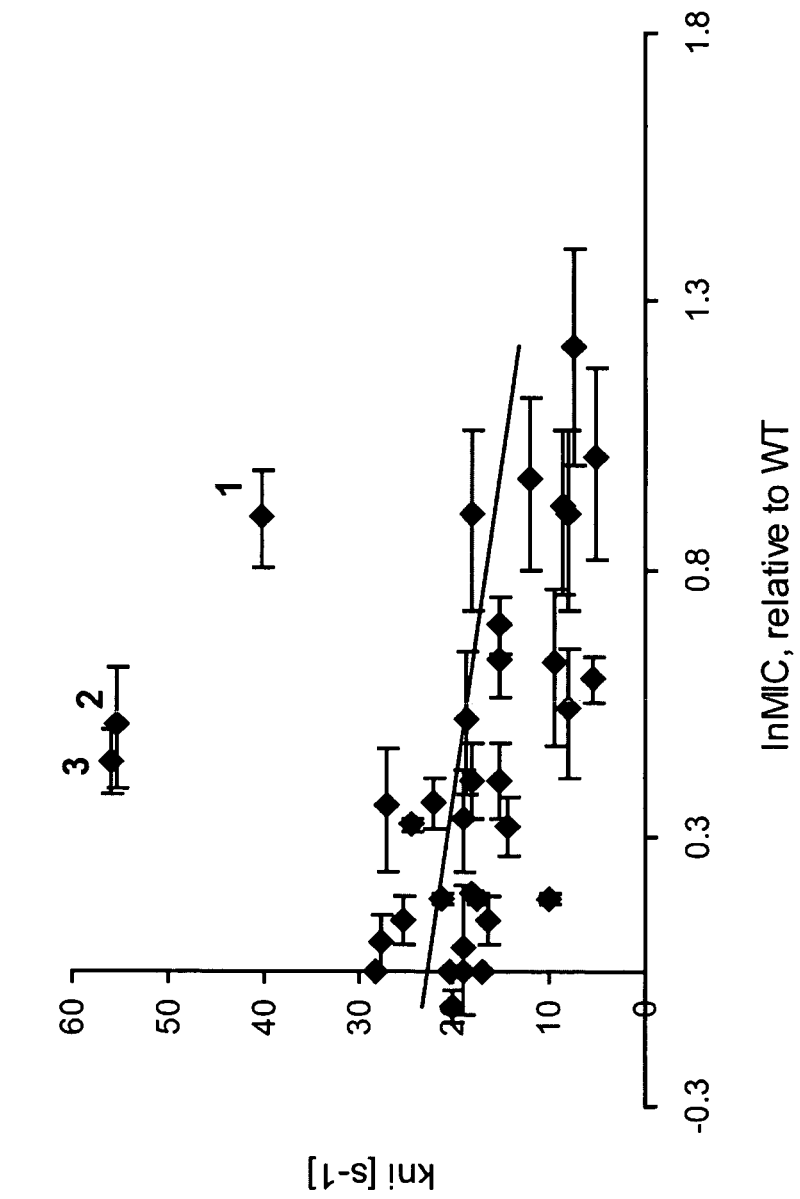
Figure 4:
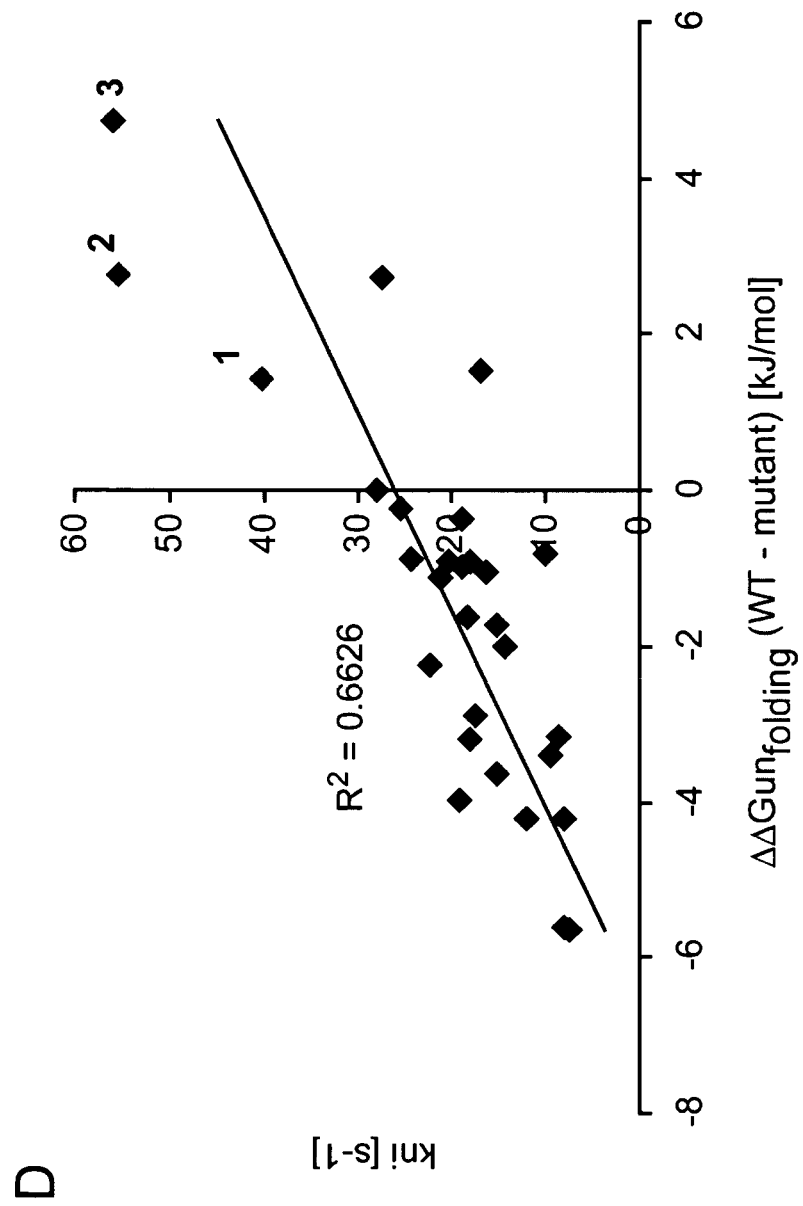

Eris was much more successful in predicting that a mutant should have a stabilizing effect, correctly predicting that the single point mutations should be stabilizing, but eris overpredicted the magnitude of the stabilizing effect massively. MIC as part of a tripartite fusion can not just be used with a high degree of accuracy to predict if proteins are thermodynamically stabilizing or not, but there is a high correlation of $R^2=0.76$ between the experimental stabilities and the MIC, showing that MIC can be used with good accuracy to predict the magnitude of the stabilizing and destabilizing effects (see FIG. 4B).

Accordingly, in some embodiments, the present invention provides methods and compositions for the in vivo or in vitro selection for expression of heterologous proteins. Exemplary compositions and methods and described in detail below.

I. Heterologous Molecules

As described above, in some embodiments, the present invention provides heterologous fusion molecules and genes encoding the fusion molecules for use in the determination of molecules stability and for identifying and selecting molecules with desired folding and stability characteristics. In some embodiments, a gene encoding a molecule of interest is inserted into a gene encoding a screenable marker or otherwise associated with the gene encoding the screenable marker so as to disrupt the function of the screenable marker to a higher degree when the molecule of interest is unstable and to a lesser degree when the molecule of interest is stable. For example, the gene encoding the molecule of interest may be inserted into the gene encoding the screenable marker in a location that permits the screenable marker to maintain at least a portion of its screenable activity. The greater the stability of molecules of interest, the more screenable activity is maintained. As such, by stressing the host cells expressing the screenable marker, the degree of stability of the molecule of interest is assessed. Thus, the compositions and methods of the present invention provide efficient systems for screening and selecting stable molecules of interest. Large libraries of candidate molecules (e.g., generated by molecular evolution or other techniques) are readily screened for members having the highest or desired stability.

A. Markers

The present invention is not limited to a particular screenable marker. For example, for insertion, all that is required is a site or sites within the screenable marker that will tolerate insertions, where the N and C termini of the insertion site are maintained at a sufficiently high local concentration for the screenable marker to function properly. Most or all of the selectable and screenable markers developed for the PCA technique find use in the methods described herein. These include a variety of protein reporters including, but not limited to, DHFR (dihydrofolate reductase), β-lactamase, green fluorescent protein (GFP) and various yellow, blue and red fluorescent proteins (YFP, CFP and RFP), *Renilla* and firefly luciferase, GAR transformylase, aminoglycoside hygrotransferase, and a variety of other reporters. In addition to these proteins the TetA protein of bacteria is a membrane bound protein that can be separated into two parts that may regain function upon their forced interaction.

Additional screenable markers are known in the art. For example, U.S. Pat. No. 6,428,951 and ISBN 0-914826-89-1 pages 990-1015 In: Frederick C. Neidhardt (ed.) *Escherichia coli* and *Salmonella typhimurium*: Cellular and Molecular Biology, ASM Press, Washington, D.C., 1986 (each of which is herein incorporated by reference) describe exemplary screenable markers. Positive screenable markers for use with mammalian cells in culture are described, for example, in Hum. Gene Ther. 1991 Fall; 2(3): 195-201 (herein incorporated by reference). Exemplary markers for use in plants are described, for example, in Miki et al., J Biotechnol. 2004 107(3): 193-232 (herein incorporated by reference).

Exemplary antibiotic resistant markers that can be used in useful in a range of organisms include, but are not limited to, Puromycin, Blasticidin S, G418/Kanamycin, Hygromycin B Phleomycin and ZEOCIN. ZEOCIN, for instance, is a formulation of phleomycin D1, a copper-chelated glycopeptide antibiotic produced by *Streptomyces* CL990. ZEOCIN causes cell death by intercalating into DNA and cleaving it. This antibiotic is effective on most aerobic cells and is therefore useful for selection in bacteria, eukaryotic microorganisms, plant and animal cells. Resistance to ZEOCIN is conferred by the Sh ble gene product which inactivates ZEOCIN by binding to the antibiotic.

In some embodiments where the molecule of interest is RNA, the screenable marker is RNA. For example, in some embodiments, the screenable marker is tRNA or ribosomal RNA.

Figure 3:
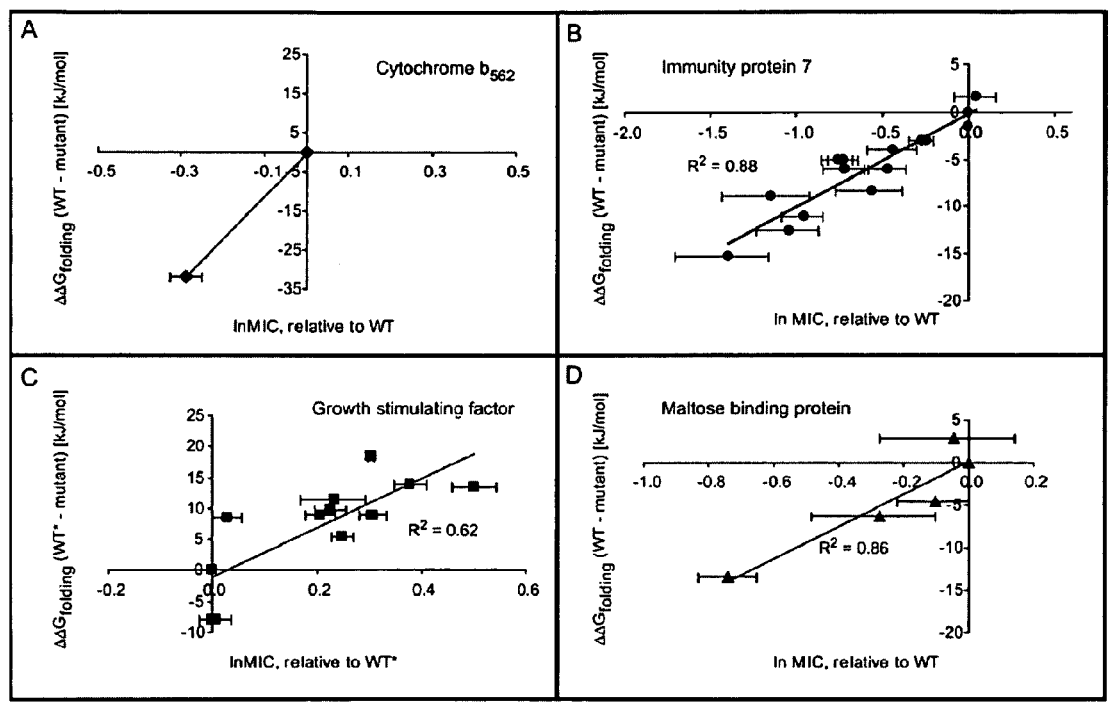
FIG. 3 shows the minimal inhibitor concentration (MIC) of penicillin V for four different proteins as well as destabilized or stabilized mutants of these proteins inserted into β-lactamase via a flexible linker.

In some embodiments, the gene encoding the β-lactamase protein is used as a selectable marker for insertion of genes encoding a protein of interest. This marker is used to illustrate embodiments of invention hereinafter. It should be understood that other markers may be used and that β-lactamase is used for convenience to illustrate exemplary uses and forms of the invention. One exemplary construct is shown in FIG. 3. In the embodiment shown in FIG. 3, genes encoding a protein of interest are inserted into the β-lactamase gene. In some embodiments, genes encoding a protein of interest are inserted in between amino acids 196 and 197 of β-lactamase. However, any insertion site that permits reconstituted activity may be used.

European patent application EP 1564286A1 (herein incorporated by reference) refers to a hybrid β-lactamase. U.S. Pat. No. 5,830,457 (herein incorporated by reference) describes the use of β-lactamase as a carrier protein for heterologous epitopes for the preparation of vaccine.

In some embodiments, the compositions and methods of the present invention are based on the expression of β-lactamase from pBR322, a moderate copy plasmid. In some embodiments, β-lactamase is expressed from two promoters (Brosius et al., (1982) J Biol Chem. 257, 9205-9210) to a sufficient amount to confer β-lactam antibiotic resistance, but not too high to cause aggregation or inclusion body formation (Bowden and Georgiou, (1990) J Biol Chem. 265, 16760-1676). Molecules to be tested are thus expressed in a moderate level without further induction. The system is very sensitive compared with other systems which may require the over-expression of the reporter protein. In some embodiments, the system is modified to overexpress β-lactamase to mimic the conditions occurring when overexpressing target proteins. Thus, the compositions and methods of embodiments of the present invention can be used to improve the expression of proteins that aggregate when overexpressed. Lack of β-lactamase activity can be due to either cleavage of the inserted protein or seeding of aggregation of the trimeric fusion protein by the inserted protein.

In other embodiments, the kan marker is employed to select E. coli as well as mammalian cells. Aminoglycoside phosphotransferases inactivates antibiotics like kanamycin, neomycin etc. in E. coli (prokaryotes) and antibiotics like G418 (Geneticin) in eukaryotic cells. Aminoglycoside phosphotransferases is expressed constitutively from high copy number plasmid under its own promoter. The APH tripartite fusion described herein as a selection marker for both prokaryotic as well as eukaryotic cells is particularly suitable for applications involving making guest proteins based on their stabilities, discovery of folding partners, and optimization of folding compartments. In the prior studies, where aminoglycoside phosphotransferases were dissected to separate N-domain domain and catalytic domain of enzyme (Michnick et al., (2000), Methods in enzymology 238, 208-30 and Paschon D. E., Patel Z. S., and Ostermeier M (2005) JMB, 353, 26-37). The protein complementation assays were used for protein-protein interactions in the cytoplasm. In another approach, aminoglycoside phosphotransferase (APH) was used as selection marker by fusing guest proteins to its N-terminus or A2-10 APH for a wide range of organisms (U.S. Pat. No. 5,116,750). A similar approach of an N-terminal fusion for APH selection marker was also employed for thermophilic bacterium (Chautard et al, (2007) Nature Methods, 4 (11) 919-921).

In still further embodiments, insertion site in the zeocin binding protein are utilized as screenable markers. Zeocin binding protein is expressed constitutively from high copy number plasmid under control of bla promoter. In another approach, a reporter protein GFP was fused at the N-terminal of Zeocin binding protein (ZBP) for screening under Zeocin pressure (Hu et al., (2004) J Virol Methods 117, 129-136).

B. Molecules of Interest

The present invention is not limited to a particular molecule of interest. Any molecule for which it is desirable to improve or alter the stability or folding may be optimized using the compositions and methods of the present invention. Any proteins, peptides, protein fragments, enzymes, immunoglobulins, and the like may be used, including but not limited to, fibrous proteins (e.g., cytoskeletal and extracellular matrix proteins), globular proteins (e.g., plasma proteins, hemoproteins, cell adhesion proteins, transmembrane proteins, hormones and growth factors, receptors, DNA-binding proteins, immune system proteins, nutrient storage/transport proteins, chaperones and the like), synthetic proteins, known or candidate pharmaceutical proteins, oxidoreductases, transferases, hydrolases, lyases, isomerases, ligases, aptamers, etc. may be used. Other structured molecules encoded by DNA may also be analyzed, including but not limited to, mRNA, tRNA, catalytic RNAs (e.g., ribozymes), and the like. Five proteins of diverse structure and function are described experimentally herein to illustrate features of the invention. Cytochrome b562, Immunity protein 7, G-CSF (neopogen), maltose binding protein and Bovine pancreatic trypsin inhibitor were tested using the β-lacatamase system described above. Therapeutic, industrial, or research proteins that are difficult to express in stable form are particularly suited to analysis and optimization using compositions and methods of the present invention. Examples of such proteins include, but are not limited to, human Tert, human Eakl and human TAP-A, Saccharomyces Vac 17, tissue plasminogen activator (tPA), rat G olf-alpha, and bovine transducin beta subunit. Recombinant tPA is used in disease which feature blood clots, such as myocardial infarction and stroke. The G alpha subunits are hard to express proteins that are very important in G protein coupled receptor signaling. The present invention is not limited to the specific molecules of interest described herein.

C. Vectors

Large numbers of suitable vectors are known to those of skill in the art, and are commercially available. Such vectors include, but are not limited to, the following vectors: 1) Bacterial: pBR322. pBAD33, pQE70, pQE60, pQE 9 (Qiagen), pBS, pD10, phagescript, psiX174, pbluescript SK, pBSKS, pNH8A, pNH16a, pNH18A, pNH46A (Stratagene); ptrc99a, pKK223 3, pKK233 3, pDR540, pRIT5 (Pharmacia); 2) Eukaryotic: pWLNEO, pSV2CAT, pOG44, PXT1, pSG (Stratagene) pSVK3, pBPV, pMSG, pSVL (Pharmacia); and 3) Baculovirus: pPbac and pMbac (Stratagene). In some embodiments the vector is replicable in multiple hosts. The pPICHOLI vectors, for example, have been designed for heterologous gene expression in the yeast P. pastoris as well as in the prokaryote E. coli. Any other plasmid or vector may be used as long as they are replicable and viable in the host. In some embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non transcribed sequences. In other embodiments, DNA sequences derived from the SV40 splice, and polyadenylation sites may be used to provide the required non transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the *E. coli* lac, trp or arabinose, the phage lambda pL and pR, T3 and T7 promoters, and the cytomegalovirus (CMV) immediate early, herpes simplex virus (HSV) thymidine kinase, and mouse metallothionein I promoters and other promoters known to control expression of gene in prokaryotic or eukaryotic cells or their viruses. In other embodiments of the present invention, recombinant expression vectors include origins of replication and screenable or selectable markers permitting transformation of the host cell (e.g., dihydrofolate reductase or neomycin resistance for eukaryotic cell culture, or tetracycline or ampicillin resistance in *E. coli*).

In some embodiments of the present invention, transcription of the DNA encoding the polypeptides of the present invention by higher eukaryotes is increased by inserting an enhancer sequence into the vector. Enhancers are cis acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome-binding site for translation initiation and a transcription terminator. In still other embodiments of the present invention, the vector may also include appropriate sequences for amplifying expression.

In some embodiments, vectors further comprise linkers for inserting the molecule of interest into the screenable marker. In some embodiments, the linkers comprise polylinkers or multiple cloning sites. In some embodiments, linkers are cleavable linkers (e.g., for removal of the molecule after expression).

D. Host Cells

In some embodiments, *Escherichia coli* (*E. coli*) is utilized as a host cell. However, the present invention is not limited to the use in *E. coli*. In other embodiments of the present invention, the host cell is a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*. In other embodiments of the present invention, the host cell is a eukaryotic cell (e.g., a yeast or mammalian cell including but not limited to *Saccharomyces cerevisiae, Schizosaccharomycees pombe, Drosophila* S2 cells, Spodoptera Sf9 cells, Chinese hamster ovary (CHO) cells, COS 7 lines of monkey kidney fibroblasts, (Gluzman, Cell 23:175 (1981)), C127, 3T3, 293, 293T, HeLa and BHK cell lines).

In some embodiments, introduction of the construct into the host cell can be accomplished by calcium phosphate transfection, DEAE Dextran mediated transfection, electroporation (See e.g., Davis et al., Basic Methods in Molecular Biology, (1986)) or other known transfection or transformation techniques.

Proteins can be expressed in mammalian cells, yeast, bacteria, or other cells under the control of appropriate promoters. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989).

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze thaw cycling, sonication, mechanical disruption, or use of cell lysing agents.

As described below, in some embodiments, the present invention provides host cells optimized for expression of stable proteins. In some embodiments, cells have altered or mutated chromosomes. In other embodiments, cells are mutaginized (e.g., irradiated, exposed to chemical mutagens, etc.) and selected/screened for enhanced ability to express constructs of the invention generally. In still further embodiments, host cells are screened for the specific expression of a particular molecule of interest or screenable marker of interest or both or all three. In some embodiments, such host cells are used as a production system to produce the stable molecule of interest.

E. Selection

The present invention also provides methods for screening for molecules and host cells that express molecules with enhanced or altered stability. In some embodiments, a gradient of selection reagent (e.g., antibiotic) or external stress is administered to cells and the ability of cells to survive in the presence of the reagent or stress is assessed. In some embodiments, the minimum inhibitory concentration (MIC) is determined. The MIC is defined as the minimum concentration of selection reagent that allows for growth of cells. The higher the MIC, the more stable the protein of interest. Proteins with higher stability can also be identified as having lower AG unfolding values. The Figures included herewith illustrate the determination of MIC and proteins with increased or decreased stability relative to the wild type protein. In some embodiments, methods to detect mutations including, but not limited to, traditional mapping PI and HfR and MutS cloning of alterations are used in conjunction with selection and screening methods.

In some embodiments, the most stable molecules are selected. In other embodiments, molecules of intermediate stability are selected. In other embodiments combination of single mutants to generate multiple mutations with further enhanced stability are selected.

F. Kits

In some embodiments, the present invention provides kits for expressing and folding molecules of interest. Kits may comprise all reagents necessary, sufficient or useful for carrying out any method herein. For example, in some embodiments, the kits contain at least one vector encoding at least a portion of a screenable (e.g., selectable) marker protein with linker sites for insertion of a gene encoding a protein of interest. In some embodiments, the kits contain all of the components necessary or sufficient to clone a gene encoding a protein of interest into the vector, as well as control plasmids, reagents, and any buffers needed for expression of a protein of interest.

In yet other embodiments, the kit further comprises components and instructions for analyzing expressed and/or purified proteins or for preparing genes expressing compounds of interest. For example, in some embodiments, the kits include components for performing protein or enzyme activity assays.

II. Applications

The methods and compositions of embodiments of the present invention described herein find use in a variety of systems. Exemplary applications are described below.

A. Modifications of Proteins of Interest

As described above, in some embodiments, the present invention provides methods of identifying variants in heterologous proteins that show superior expression and stability. Because the methods of the present invention can be performed in vivo, it is not necessary to know details about the structure of the proteins in order to perform the method.

In some embodiments of the present invention, the selection and screening methods are used to improve the stability of wild type proteins. In some embodiments, a series of variant proteins are generated and then assayed for stability using the methods of the present invention. Variants with increased stability are thus identified. In some embodiments, large-scale mutagenesis of the heterologous protein gene to find rare mutations that enable superior expression of the heterologous protein is performed. Methods of mutagenesis include, but are not limited to, error prone PCR, use of mutator strains, chemical mutagensis, random insertion and deletion mutagenisis, random oliognucleotide mutagensis, saturation mutagenesis, DNA shuffling, creation of hybrid protein libraries. Examples of mutagenesis methods are described in Methods in Molecular Biology volume 231 "Directed Evolution Library creation" ed FH Arnold and G Georgiou. In some embodiments, stable domain boundaries within proteins are determined by a progressive deletion approach followed by the screening methods of embodiments of the present invention (See e.g., IEEE Trans Nanobioscience. 2008 June; 7(2):172-81; herein incorporated by reference in its entirety).

In some embodiments, already mutated proteins are used as a starting point from which to improve stability. In some embodiments, variants comprise amino acid changes. In some embodiments, amino acid changes or other modifications are used to alter or add salt bridges, disulfide bonds, or hydrophobic interactions.

In some embodiments, screening is performed in a high-throughput manner. This allows for the screening of large numbers of protein variants without knowing where the mutations are located. In some embodiments, high throughput systems utilize robotics. The use of robotics enables the steps of cloning and expression optimization to be carried out quickly and efficiently. In some embodiments, the high throughput protein lab uses ligation-independent cloning (LIC) for rapid and simultaneous creation of multiple different constructs. The ligation and restriction digestion steps associated with conventional cloning are unnecessary in LIC. In some embodiments, a 96 well format (or other plate format) is used in high throughput screening.

In some embodiments, the compositions and methods of the present invention are used to optimize the expression of cytosolically located proteins. In other embodiments, the compositions and methods of the present invention are used to optimize the expression of exported proteins.

In some embodiments, the compositions and methods of the present invention are used to optimize the expression of membrane proteins. The expression of membrane bound proteins is particularly problematic. The compositions and methods described herein find use in the optimization of stability of membrane bond proteins (e.g., where the N and C terminal ends are located in the non-cytosolic compartment), as the periplasmic compartment is where β-lactamase is normally expressed. In some embodiments, addition of appropriate transmembrane linkers onto the existing gly-ser linkers in the β-lactamase constructs enables the expression of membrane bond proteins with any particular trans-membrane topology.

In some embodiments, other linkers and insertion sites within β-lactamase, and mutants that stabilize or destabilize β-lactamase or allow it to ability to confer resistant to other β-lactam antibiotics allow one to fine tune the system for various purposes, including selection of stabilizing mutations in proteins over 100 kD.

In further embodiments, the compositions and methods of the present invention are used with an appropriate screenable RNA marker to select stabilized variants of any RNA, which is useful for a variety of purposes. For example, RNA instability is a major bottleneck in gene expression. The methods described herein enable one to select for more stable and thus better expressing RNA constructs.

B. Modification of Host Cells

The present invention is not limited to the selection of variant molecules of interest with improved stability. In some embodiments, the methods and compositions described herein are utilized to identify variants in the host cells that have an enhanced ability to promote the folding of heterologous molecules. Those variants in the host strain that enable high levels of expression of the heterologous protein may be resistant to high levels of selective stress. In some embodiments (e.g., optimization of pharmaceutically relevant protein) it is desirable not to modify the sequence of the protein itself. This avoids allergy concerns and the potential need to obtain FDA approval for the altered protein. In this case, the system described herein allows one to select for variants of the host cell that enable more efficient folding of the target protein. These mutants can be made, for example, by targeting folding factors (e.g., protein disulfide isomerases) and chaperones (e.g., GroEL), for mutagenesis.

In some embodiments, by mutating the host chromosome, it is possible to generate an expression (e.g., *E. coli*) strain that is optimized for the expression of a certain target protein, or as a general expression strain. For instance, if the host cell is generally not very effective in folding proteins that contain multiple disulfide bonds, including many proteins of pharmaceutical importance, one could start by inserting a protein that contains multiple disulfides into β-lactamase and then select for variants in the host chromosome or in bacterial enzymes involved in disulfide bond formation that simultaneously enable high levels of resistance to β-lactam antibiotics and thus allow the effective expression of other heterologous proteins that contain multiple disulfide bonds. These stains provide good candidates for those that would provide the expression of a wide variety of disulfide containing proteins. Use of host bacterial mutants that alter the stability of proteins or their ability to fold, such as strains that overexpress proteases, or eliminate chaperones and folding factors increase the effective range of the selection.

In some embodiments, by fusing β-lactamase constructs with a twin arginine (Tat) signal peptide (such as ssTorA of the *E. coli* trimethylamine N-oxide reductase (TorA)) instead of β-lactamase's normal signal sequence, it is possible to select for proteins that have to fold in the cytoplasm, instead of the periplasm. As a result of the folding quality control feature of the Tat pathway, only folded proteins are competent for export via the Tat transporter (DeLisa et al., (2003) Proc Natl Acad Sci USA. 100, 6115-6120). Thus only when the inserted protein is properly folded, β-lactamase with the inserted protein can be secreted into periplasm through the Tat transporter and confer β-lactam antibiotic resistance. The Tat pathway also tolerates the secretion of proteins of larger size. The compositions and methods described herein enable the selection of variants in the host chromosome or in bacterial chaperons that improve the folding of a cytoplasmic protein inserted into β-lactamase. Investigation of the effect of reducing and oxidizing environment of folding behavior of a protein is possible by expression of the β-lactamase in the cytoplasm and separately in the periplasm.

The compositions and methods described herein are not limited to monitoring protein stability in bacteria but can be used in any organism in which one can introduce exogenous DNA. Well developed expression systems exist in bacteria other than *E. coli*, yeast, baculovirus/insect cell lines, and mammalian cell lines. Other model organisms into which DNA can be introduced include, but are not limited to, *S. pombe* (fission yeast), *Neurospora, C. elegans, D. melanogaster, D. rerio, Xenopus*, mouse, and rat. β-lactamase complementation assays have already been established for mammalian cells.

C. Uses of Expressed Proteins

Proteins expressed and purified using the compositions and methods of the present invention find use in a variety of applications, including, but not limited to, those disclosed herein. Once an optimized molecule and/or host cell is identified, the optimized systems may be configured for high level expression of the molecule of interest. For example, in some embodiments, an optimized protein is moved to a commercially available system designed for high level expression of therapeutic, industrial, or research proteins.

In some embodiments, the compositions and methods of embodiments of the present invention find use in improving the production of protein and peptide drugs. Producers of candidate protein and peptide drugs include, but are not limited to, Amgen, Biogen-IDEC, Iio, Chiron, Genzyme, Genentech, Serono, Aventis, Eli Lilly, Johnson & Johnson, Zymogenetics, and Novo Nordisk.

In certain embodiments, compositions and methods of embodiments of the present invention find use in drug screening methods (e.g., to screen for inhibitors of proteolysis or protein aggregation). There are many diseases that are due to protein aggregation (e.g., including but not limited to, Alzheimer's disease, prion diseases, and type II diabetes).

In further embodiments, the compositions and methods of embodiments of the present invention find use in stable domain mapping to identify stable domains of proteins.

In other embodiments, the present invention provides methods for improving the high throughput determination of crystal structures for research purposes and drug discovery. Many techniques for studying protein structure are known in the art and include, but are not limited to, X-ray crystallography, spectroscopy (e.g., UV or Infared spectroscopy), and mass spectrometry.

In yet other embodiments, the present invention provides methods for improving the expression of proteins for research purposes. For example, in some embodiments, proteins are utilized in studies of protein function. Such studies include, but are not limited to, assays of enzymatic activity and interaction with a ligand or substrate or other molecule. Methods for performing such assays are known to one of skill in the art.

In still further embodiments, the present invention provides methods for improving the production of industrial enzymes. Major classes of industrial enzymes include; carbohydrases, proteases, and lipases. The major end-uses are in food feed, detergents, textiles, leather, and pulp & paper. Companies involved in industrial enzymes include, but are not limited to, AB Enzymes GmbH, Advanced Enzyme Technologies Ltd., Aureozyme Inc., Biocon India, BioResource International (BRI), Chr. Hansen, Danisco A/S, Genencor International, Inc., DIREVO Biotech AG, Diversa Corporation, DSM, Enchira Biotechnology Corporation, Enzymatic Deinking Technologies LLC, Genencor International, Inc., KBI BioPharma, Inc., Maxygen, NEXGEN Biotechnologies, Inc. and Novozymes A/S.

EXPERIMENTAL

The following examples are provided in order to demonstrate and further illustrate certain preferred embodiments and aspects of the present invention and are not to be construed as limiting the scope thereof.

Example 1

This Example utilizes the properties of a tripartite fusion where the gene for the heterologous protein is inserted into a gene that encodes a screenable or selectable phenotype.

Materials and Methods

Plasmid Construction:

*Escherichia coli* strain NEB10beta was used for both cloning and expression purposes. For the expression of tripartite fusions between β-lactamase and Im7 or cytochrome b562, a flexible 30-amino-acid linker (GGGGS)$_2$SSGSGSGSGS (GGGGS)$_2$ (SEQ ID NO:1) was introduced between position 196 and 197 of TEM1-β-lactamase encoded by the vector pBR322. Recognition sites for PfoI and a Bsu36I in approximately the middle of the linker encoding region allowed the insertion of guest protein genes.

To eliminate a unique PfoI site within pBR322, the plasmid was linearized with PfoI and the resulting sticky ends filled in with Klenow enzyme. After phosphorylation the plasmid was recirculized by ligation, resulting in the derivative pBR322*. For the insertion of a linker encoding region at position 588 of the bla gene, primers 5'CCGCTCCCGGAACCTGAGGAA-GAACCACCACCACCAGAACCACCACCACCTAGTT CGCCAGTTAATAGTTTGCGCAACGTTGTTGCC3' (SEQ ID NO:2) and 5' AAGTGGGAGCGGAGGCGGCG-GATCAGGCGGAGGTGGAAGCT-TGACTCTAGCTAGCC GGCAGCAGCTCATAGACTGGATGGAGGCG3'(SEQ ID NO:3) were used to amplify the vector pBR322* in a whole plasmid PCR. Here, the 5' part of each primer encoded for the first 7 (primer 2) or last 14 (primer 1) amino acids of the GS linker. The remaining nucleotides of each primer were complementary to the regions directly upstream (primer 2) or downstream (primer 1) of the insertion site within the bla gene. The resulting linear PCR product was phosphorylated and recirculized by ligation, resulting in the vector pBR322*link. The Im7 and the cytochrome b562 gene were amplified from plasmid or chromosomal *Escherichia coli* NEB10beta DNA, respectively, and cloned into pBR322*link using PfoI.

For the expression of tripartite fusions between β-lactamase and gcsf or MBP, the bla-gene with the linker encoding region was amplified from pBR322*link and cloned into pBAD43 with EcoRI and XbaI. A whole plasmid PCR of the resulting vector pBAD43-bla-link with the primers 5'GTTC-CGGAAGCGGAGGAGGTGGTTCAGGCGGAGG3'(SEQ ID NO:4) and 5' CGCTCCCGGATCCTGAGCTCGAGC-CACCAC3'(SEQ ID NO:5) was performed to introduce additional restriction sites for the insertion of guest protein genes without altering the amino acid sequence of the β-lactamase and the linker (pBAD43bla-link*). A codon-optimized version of the gcsf gene was synthesized in vitro and cloned into pBAD43bla-link* using XhoI and PfoI. For the expression of the β-lactamase-MBP fusion, a 64 amino-acid long GS-linker was introduced into the bla gene as described for pBR322*.

Whole plasmid PCR was performed using pBAD43bla-link as a template and primers 5'CGGGAGCGGGAGCTCT-TCTGGTTCCGGAGGCGGTGGAGGATCAG-GCGGTGGCGGA TCAGGAAGTGGGAGCGGAGGCG-GCGGATCAGGCGG3'(SEQ ID NO:6) and 5' GAACTCGAGCCACCGGATCCTGAGCCAC-CACCACCAGATCCCCCGCCACCTGAACC TGAG-GAAGAACCACCACCACCAGAACCACC3'(SEQ ID NO:7) and resulted in the generation of the vector pBAD43-bla-link_long. The malE gene was amplified from the vector pMAL-2p and ligated into pBAD43bla-link_long. Point mutations of the genes inserted into the bla gene were generated by using the QuikChange-II-Site-Directed-Mutagenesis-Kit (Stratagene). All constructs were verified by sequencing.

Effective Linker Lengths after Cloning of Inserts
pBR322*link-Im7: 32 aa
pBAD43link_new_MCS-gcsf: 28 aa
pBAD43link_long-MBP: 67 aa
pBR322*link-cyt: I guess 32aa,
pBR322*link: 30 aa
pBAD43link_new_MCS: 30 aa
pBAD43link_long: 67

Testing of Antibiotic Resistance:

Spot titer tests were performed to determine the level of antibiotic resistance of cells expressing β-lactamase tri partite fusions. Mid-log phase cells of *Escherichia coli* NEB10beta were adjusted to A600=1 and serially diluted in sterile 170 mM NaCl solution. 2 µl of each dilution was spotted onto LB plates supplemented with increasing concentrations of Penicillin V. After incubation at 37° C. for 18 h the minimal concentration of Penicillin V where cell growth could still be detected was determined for cell dilutions of $10^{-1}$, $10^{-2}$ and $10^{-3}$. This concentration was defined as the minimal inhibitory concentration (MIC) for a given cell dilution. The MIC values were normalized to the MIC for Im7 WT and averaged.

Preparation of Libraries and Selection for Mutants Leading to Increased Levels of Antibiotic Resistance:

Mutagenesis of the Im7 gene was performed by the MEGAWHOP technique described previously with minor modifications. In the first PCR round, Mutazyme II® enzyme (Stratagene) was used to amplify the Im7 WT gene from pBRlink-Im7 WT using primer 5' ATGGAACTGAAAAAT-AGTATTAGTG3'(SEQ ID NO:8) and 5'GCCCTGTT-TAAATCCTGG3'(SEQ ID NO:9), which are complementary to the 5'- and the 3'-end of the Im7 gene. The cycle was 95° C. 2 min, 54° C. 1 min, 72° C. 1 min, repeated 35 times, using 0.1 to 100 ng of the target region. The resulting PCR product was analyzed on a 1.5% agarose gel and the amplicon band excised from the gel and purified using the Qiaquick gel extraction kit (Qiagen). About 200 ng of this mutant DNA was used in a second PCR round to replace the Im7 Wt gene in pBRlink-Im7 WT. The cycles for the second PCR were 95° C. 2.5 min, 55° C. 1 min, 72° C. 12 min, repeated 30 times, using 5 U of the high-fidelity polymerase Pfu Turbo® polymerase (Stratagene) and 50 ng dam-methylated template plasmid. Afterwards, 20 U DpnI were added to the PCR reaction and the reaction was incubated at 37° C. for 4 hours in order digest the dam-methylated parental plasmid DNA. The undigested PCR product was precipitated using pellet paint (Novagen) and resuspended in 5 µl H2O. 2 µl of this library were transformed into chemically competent NEB10beta cells and subjected to selection on LB Penicillin V plates. The template plasmid for the random mutagenesis, pBRlink-Im7 WT, served as a control in a second transformation reaction. After incubation overnight at 37° C., single colonies of the library were picked from plates containing PencillinV concentrations that didn't allow any cell growth for pBRlink-Im7 WT. The mutated plasmid DNA was isolated, sequenced, and retransformed into fresh NEB10beta cells. Spot titer tests were performed to determine the relative increase in antibiotic resistance of the mutations in Im7 compared to wild type Im7, and to verify that the increase was caused by alterations in Im7 instead of alterations in the bacterial expression strain.

Determination of Expression Levels:

For the whole cell extracts, 1 ml of mid-log phase cells were pelleted and adjusted to A600=5 in 1×PBS, 2 mM EDTA. After adding of 5× reducing loading dye, the extracts were boiled for 10 min. Protein samples were subjected to SDS-polyacrylamide electrophoresis and transferred to nitrocellulose membranes. The membranes were blocked for 1 h in TBS, 5% milk powder, washed 3×10 min and incubated overnight with rabbit anti-β lactamase polyclonal antibody (Chemicon, dilution 1:10,000) at 4° C. After three washing steps (10 min each), the membranes were incubated with HRP-Goat Anti-Mouse IgG antibody (Zymed Laboratories, dilution 1:2,500) for 2 h. The membranes were washed 3×30 min and the secondary antibody detected with SuperSignal West Pico Chemiluminescent Substrate as described by the supplier (Pierce). The β-lactamase antibody was removed by incubating the membranes in stripping buffer (0.2 M Glycin, 0.1% SDS, 1% Tween 20, pH 2.4) for 2 h. The detection of the internal standard MBP was performed as described above using anti-MBP monoclonal antibody (NEB, dilution 1:10.000) as a primary and HRP-Goat Anti-Mouse IgG (Zymed Laboratories, dilution 1:2,500) as a secondary antibody.

All washing steps were performed with TBS-T (0.1% Tween 20), all antibodies were diluted in TBS, 5% milk powder.

Expression of Im7 Mutants for Thermodynamic Characterization:

Im7 constructs were cloned into pTRC-99 vectors for expression in *E. coli*. The mutant proteins were expressed as a his6 fusion as described previously. Proteins were expressed in JM83 *E. coli* grown in LB media. Expression was induced with IPTG and cells harvested after four hours. Cells were lysed by sonication and the soluble proteins purified by Ni affinity chromatography (Peirce Pro-Pure IMAC spin columns) and further purified on Q-Sepharose columns. Pure protein was dialyzed into water and lyophilized for storage.

Equilibrium Unfolding Experiments:

Proteins were dissolved to a concentration of approximately 100 µM in 50 mM Tris-Cl buffer at pH 7.5, containing 400 mM $Na_2SO_4$. Substocks of each mutant were made up in the same buffer containing 0, 2, 4, 6 and 8 M urea. These substocks were titrated into a black polypropylene 384 well microtitre plate (Greiner) to create eight replicates of a urea titration from 0 to 8 M urea in steps of 0.2 M urea, using a Hamilton Microlab Star robot. The plates were briefly centrifuged and incubated at 37° C. for one hour to allow the unfolding reaction to come to equilibrium. The tryptophan fluorescence of each sample was measured using a PerkinElmer EnVision platereader. The excitation wavelength was 280 nm and emission was measured using a 340-350 nm filter. Data were normalized and processed using Igor Pro (Wavemetrics). The entire dataset was fitted globally to a two-state equilibrium unfolding equation and the ΔG values for each Im7 variant were compared to that of the wildtype protein under identical conditions. ΔΔGUN=ΔGUN(mutant)−ΔGUN(wildtype)

Kinetic Unfolding Measurements:

Proteins were dissolved in 50 mM Tris-Cl buffer at pH 7.5, containing 400 mM $Na_2SO_4$. Each protein was rapidly unfolded by mixing with the same buffer containing 7.7 M urea to give a final urea concentration of 7 M, using an Applied Photophysics SX18-MVR stopped flow fluorimeter. The change in tryptophan fluorescence of the proteins was measured for 200 ms at 37° C. The excitation wavelength was 280 nm and a 330 nm long pass filter was used to monitor emission. At least eight kinetic transients were averaged, and the data fit to a single exponential function using the manufacturers' software. The rate of unfolding in the absence of urea was extrapolated by assuming that the m-value for the transition was the same as that measured for the wildtype protein. The rate Kni was determined, although this is actually the rate at which Im7 unfolds to the intermediate form, since this is the rate limiting step in Im7 unfolding, Kni is approximately the same as the overall unfolding rate.

In Vivo Colicin Activity Measurements:

E. coli JM83 cells transformed with a plasmid carrying the mutant Im7 gene were used to inoculate 0.7% LB agar, which was poured onto precast 1.5% LB agar lanes in a 22 cm×22 cm plate. Once the agar had set, a serial dilution of E7 colicin (10 to 10-9 mg/ml) was spotted onto the lanes and the cells were allowed to grow overnight at 37° C. Plaques in the bacterial lawns indicated where the cells were killed by the applied colicin, and the maximum concentration of colicin at which the cells could survive was measured. Wildtype Im7 was used as a positive control, as cells expressing this protein could survive the maximum concentration of applied colicin. Cells transformed with an empty pTRC-99a vector, which showed no resistance to colicin, served as a negative control. Purified E7 colicin was from Professor Colin Kleanthous, University of York, UK.

Results

This Example describes the development of a genetic selection for improving protein stability. Such a selection allows one to explore how protein stability is determined and has many practical applications. The system developed is based on a tripartite fusion approach whereby the test protein is fused into the middle of an antibiotic resistance protein. The folding of the antibiotic resistance marker is linked to the folding of the test protein.

The antibiotic resistance marker used was TEM1-β-lactamase, which is encoded in many commonly used cloning vectors. This protein is tolerant towards insertions, deletions and substitutions that occur in a surface exposed loop in its 3D structure around amino acid 197 (Barany, Gene. 1985; 37(1-3):111-23, Hallet et al., Nucleic Acids Res. 1997 May 1; 25(9):1866-7; Zebala et al., Gene. 1991 April; 100:51-7; Barany, Proc Natl Acad Sci USA. 1985 June; 82(12):4202-6).

It was contemplated that if one inserted a single protein into this position of β-lactamase, one could use β-lactamase activity as a measure of whether or not the inserted protein stays intact in vivo. Since protease resistance is a good measure of protein stability (Park et al., J Mol Biol. 2007 May 18; 368 (5):1426-37; Parsell et al., J Biol Chem. 1989 May 5; 264 (13):7590-5), antibiotic resistance was used as a direct, and selectable readout for the stability of the inserted protein.

The tripeptide fusion approach is shown in FIG. 1. If the protein that is inserted into β-lactamase folds poorly or is unstable, it is prone to degradation. Degradation of the heterologous protein separates the N- and the C-terminal part of β-lactamase, inhibiting the folding of β-lactamase. Cells expressing such a fusion construct are sensitive towards beta-lactam antibiotics. If, on the other hand, the inserted protein folds properly and is stable, the two parts of β-lactamase will be close enough together to associate. The folding of the inserted protein thus acts to drive the folding of β-lactamase. Cells expressing this fusion construct are antibiotic resistant, a selectable phenotype.

To test the tripartite fusion approach, four different proteins were chosen for insertion, namely, Im7, cytochrome B562, G-CSF and maltose binding protein. These proteins were picked because all have stability mutants available with clearly defined thermodynamic stabilities. Im7 is a small helical protein with a well studied folding pathway that confers immunity to bacterial colicin E7. It binds very tightly to the toxic nuclease colicin E7 and in doing so inhibits its action, allowing the bacteria producing Im7 to survive (James et al., Microbiology. 1996 July; 142 (Pt 7): 1569-80). In contrast to Im7, which has no cofactors or disulfides, cytochrome B562 contains a heme cofactor (Kamiya et al., Protein Eng. 2001 June; 14(6):415-9). G-CSF is a eukaryotic protein containing three disulfides that stimulates bone marrow growth (Bishop et al., J. Biol. Chem. 2001 Sep. 7; 276 (36):33465-70. Epub 2001 Jun. 13). Maltose binding protein at 43 kD is substantially larger in size than the other three proteins (Im7: 9.9 kDa, cyt 11.8 kDa, gcsf: 18.7 kDa, MBP: 40.7 kDa). Thus the 4 proteins chosen span a variety of protein types.

Figure 2:
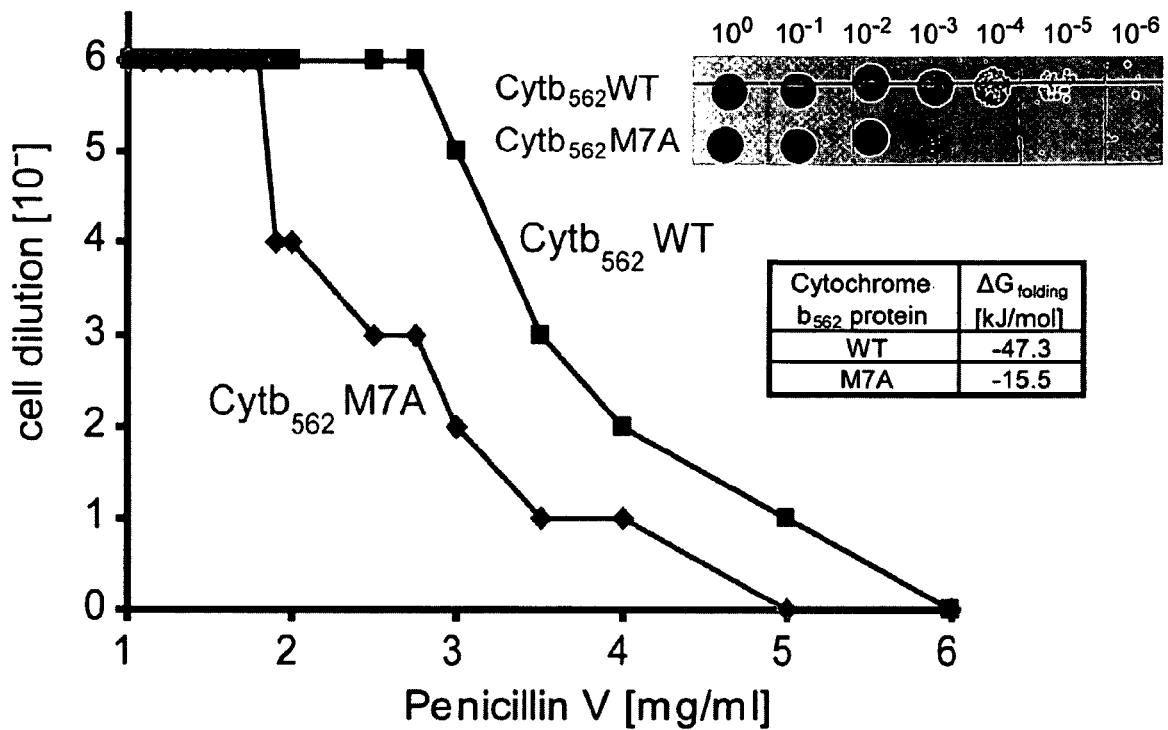
FIG. 2 Mid-log phase cells of E. coli NEB10 beta expressing β-lactamase with wild type cytochrome B562 or cytochrome B562 M7A as an insertion.

Variants of TEM1-β-lactamse that contain glycine serine linkers inserted between codon 196 and 197 of β-lactamase were constructed. These linkers were engineered to contain several restriction sites and the four test proteins were cloned into this linker to generate tripartite fusions. Derivatives of these fusions that contained mutations that are known to alter the stability of the test proteins were constructed by site specific mutagenesis. To monitor antibiotic resistance, dilutions of strains containing the various tripartite fusions were spot titered onto plates containing various concentrations of the β-lactam antibiotic penicillin V. One such spot titration that compares the growth of a fusion that contains wild type cytochrome b562 with that of a fusion that contains the destabilizing cytochrome mutation M7A on 2.5 mg/ml penicillin V can be seen in the insert to FIG. 2. The destabilized mutant is more sensitive to penicillin over a wide range of antibiotic concentrations. The minimal inhibitor concentration (MIC) of Penicillin V determined as described in the materials and methods was used as a quantitative measure of antibiotic resistance. The mutants shows only 75% of the antibiotic resistance, compared to the WT as defined by the minimal inhibitory concentration (FIG. 2 and FIG. 3A).

Using the same protocol, the MIC for wild type immunity protein 7 and a wide variety of mutants with altered stability was determined. A very good correlation $R^2=0.89$, existed between the thermodynamic stability of the published Im7 mutants, and the in vivo penicillin V resistance that they exhibit once inserted into β-lactamase as reflected by the MIC. The higher the stability of the individual mutants is, the higher is the resulting level of antibiotic resistance (see FIG. 3B). The vast majority of the previously isolated mutants were destabilized and were less resistant to penicillin V than wild type. One of the previously isolated Im7 mutants, (V27A, shown by a green dot on FIG. 3B), is more stable than wild type and results in a higher level of antibiotic resistance.

Designing stabilizing alternations in proteins is difficult. As a result, stabilizing mutations exist only for relatively few well-studied model proteins or for proteins for which there is a pressing practical need. In this latter category is granulocyte-colony stimulating factor (or G-CSF), which, under the trademark names of Neopogen and Neulasta, is used to treat cancer and AIDS patients. The wild type protein has a high tendency to aggregate, and needs to be stored under special conditions. The stability problems associated with the wild type G-CSF protein contributes to its retail price of $500,000-$1,170,000/gm. Despite its high cost, G-CSF is effective, and $4.28 billion dollars of this drug were sold in 2007. A number of stabilizing mutations in G-CSF have been designed (Ferguson et al., J Mol Biol. 1999 Mar. 12; 286(5):1597-608). It was found that the antibiotic resistance of tripartite fusions containing these mutant G-CSF correlates well with their folding free energies $R^2=0.62$ (see FIG. 2C). The fourth protein tested, maltose binding protein, was used because it is larger in size than the other 3 proteins, and its N and C termini are 44 Å apart, much more separated than the N and C termini that are visible in the crystal structure of either Im7 (21 Å) or G-CSF (33 Å). For maltose binding protein there is again an excellent correlation ($R^2=0.86$), between the antibiotic resistance of tripartite fusions containing these maltose binding protein mutants.

The above data show that the system can be used to obtain an in vivo readout for the folding free energy for proteins of various sizes, from both bacterial and eukaryote sources and with and without cofactors, or disulfides. Since the readout is resistance to antibiotic, an easily selectable phenotype, the next experiment was to select for mutations with a greater antibiotic resistance and to see how the folding properties of the inserted proteins have changed. Mutations in Im7 that show improved MIC values were identified. The Im7 portion of the fusion cloned into pBR322 was subjected to error prone PCR using the megaprimer technique (Miyazaki et al., Biotechniques 2002 November; 33(5) 1033). The mutagenized plasmids molecules were then transformed into bacterial strains. Colonies that showed resistance to higher levels of antibiotic were selected by plating on solid media that contained various concentrations of penicillin V and the DNA corresponding to the entire tripartite fusion was sequenced. Although only the Im7 portion of the fusion was targeted for mutagenesis, the entire fusion protein was sequenced to screen out mutations that had a higher resistance to penicillin because they affected the protein coding region of β-lactamase.

With the selection system, single mutations, which led to higher levels of antibiotic resistance with MIC values, were increased up to 1.5 fold. In order to see if multiple mutants or combinations of these single mutants could lead to even higher levels of antibiotic resistance, DNA from these single mutants was pooled and error prone PCR was performed on the mixed DNA sample. This allows in vitro recombination to occur between the single point mutations and also the addition of new mutations within Im7 that enhance the penicillin V resistance of any of the single point mutants. The former process was more efficient, 15 double and triple mutations were isolated that had MIC values up to 3.21, nearly all of these could be attributed to recombination between the initially isolated single mutants.

The Protein Level of the Tripartite Fusion Correlates Well with Antibiotic Resistance:

The present invention is not limited to a particular mechanism. Indeed, an understanding of the mechanism is not necessary to practice the present invention. Nonetheless, it is contemplated that possibilities underlying the increases in antibiotic resistance observed include increases in the level, specific activity, solubility, or protease resistance of the tripartite fusion protein, due to improvements in the thermodynamic stability or folding kinetics of the inserted protein.

When the steady state level of the tripartite fusion protein was measured with quantitative western blots using β-lactamase antibody, a good correlation $R^2=0.66$ between the level of the fusion protein present and MIC of penicillin V was found. This indicated that it is the level of the fusion protein present that largely determines the degree of antibiotic resistance conferred by the fusion. Mutants that have a 2 fold increased MIC showed a 3.64 fold increased expression level. This shows that one can use the system described herein to directly select for enhanced protein expression.

It was investigated whether mutants with enhanced antibiotic resistance had higher steady state levels because of enhanced stability of the Im7 portion of the fusion. Other possible explanations for enhanced antibiotic resistance include effects on the transcription or translation of the fusion, effects on the solubility or localization of the fusion or other fusion related effects, such as the mutants having effects on the catalytic properties or stability of β-lactamase itself. The only changes in these constructs are to the Im7 portion of the fusion, making transcriptional and translational effects unlikely. All of the β-lactamase of all of the Im7 mutants was in the soluble fraction and all was in the periplasm showing that the mutants did not affect the solubility or localization of the fusion. The long length and flexible nature of the linker joining the inserted protein to β-lactamase was designed to minimize non-covalent interactions between β-lactamase and the inserted protein. β-lactamase has a single disulfide, raising the possibility of interfering disulfide bond formation for those inserted proteins that contain cysteine residues. The relationship between antibiotic resistance and thermodynamic stability observed for G-CSF, a protein with 2 disulfides, indicates that disulfide bond containing proteins can function in the system.

To investigate if the changes in antibiotic resistance can be attributed to changes in the Im7 portion of the fusion, the in vitro properties of the Im7 mutants were examined in the absence of the fusion. The Im7 mutants were constructed by oligo directed mutagenesis in a standard Im7 expression system. The Im7 mutant proteins were overexpressed, purified to homogeneity by nickel affinity chromatography, and then analyzed. The analysis was designed to provide a selection for enhanced vivo protease resistance. In vitro protease resistance of the purified mutant Im7 proteins was assayed by subjecting them to a short pulse of protenase K. >80% of the mutants selected by their superior MIC values had a better in vitro protease resistance than wild type. The present invention is not limited to a particular mechanism. Indeed, an understanding of the mechanism is not necessary to practice the present invention. Nonetheless, it is contemplated that the enhanced protease resistance of the mutants is due to enhanced thermodynamic stability, enhanced kinetic stability or both. The system described herein finds use in the investigation of the determinants of in vivo stability. The folding free energy of these proteins was measured by using urea denaturation in an automated 96 well format. A good correlation ($R^2=0.76$) existed between the thermodynamic stability of the mutant proteins and the antibiotic resistance they confer in vivo as part of the tripartite fusion (FIG. 4B). 80% of the selected mutants were thermodynamically more stable than the wild type. This is an unexpected result for several reasons. For example, finding thermodynamically stabilized mutants in a target protein is usually very challenging, illustrated by the fact that of the hundreds of mutants previously isolated in the Im7 protein, only one (V27A), was more stable than wildtype. The present system can be used to select mutations with enhanced thermodynamic stability by mutagenizing and selecting for higher antibiotic resistance. The result is further unexpected because it is not just thermodynamics, but also kinetics of folding that affects in vivo stability.

Unfolded Im7 shows higher tryptophan fluorescence than folded Im7, allowing for a measurement of the unfolding rate.

It was found that the vast majority (31/34%) of the mutants selected by their enhanced antibiotic resistance values unfold more slowly than wild type (FIG. 4C). This indicates that it is not just the thermodyamics of folding that determines in vivo stability; the unfolding rate also plays a role.

In order to get a better picture of the relative contributions of thermodynamic and kinetic stability to improved MIC values of the mutants, Kni vs DeltadeltaG was plotted. On this plot the vast majority of the mutants are in the lower left quadrant, indicating that they are BOTH thermodynamically more stable than wild type AND have a slower unfolding rate. Since the delta G is a measure of the folding equilibrium, which in turn is a measure of the relative contribution of the folding and unfolding rates, it is to be expected that many proteins that show an improved thermodynamic stability will also show slower unfolding rates. The complete absence of mutants that have only an improved thermodynamic stability in the absence of a decreased unfolding rate, and the fact that nearly all of the mutants show a decreased unfolding rate, points to the importance of unfolding rates in determining the thermodynamic stability of proteins and their in vivo stability. Thus the higher MIC of nearly all of the mutants can be explained because they are both thermodynamically more stable than wild type, and exhibit a slower unfolding rate. One mutant (L19I) is less stable than wild type but exhibits a large decline in its unfolding rate, which may compensate for its lower thermodynamic stability. There are only three mutants that have both a lower thermodynamic stability and a faster unfolding rate than wild type. They are shown as numbered dots in FIG. 4 V33E (#3), V33E-D63N (#1) and N26K-D49N-S58R (#2). The V33E mutation has a higher antibiotic resistance but a lower expression level when present in the tripartite fusion, and is destabilizing, and protease sensitive when present in the isolated Im7 protein. The present invention is not limited to a particular mechanism. Indeed, an understanding of the mechanism is not necessary to practice the present invention. Nonetheless, it is contemplated that it may lead to an interaction with the β-lactamase fusion partner that altars its specific activity. The thermodynamic stability of the V33E-D63N double mutant is approximately an additive combination of the thermodynamically stabilizing effect of the D63N single mutant and the very thermodynamically destabilizing effect of the V33E mutation. The N26K-D49N-S58R triple mutant is thermodynamically less stable than wt and unfolds more rapidly and is more protease resistant than wt protein in vitro. A number of triple mutants that contain the N26K-S58R background are very stabilizing.

When the distribution of the stabilizing mutations on the crystal structure of Im7 was analyzed, many of them clustered around the binding site for colicin E7 with which Im7 binds to with picomolar affinity. Nearly half (8/19) of the single mutants mapped to residues that are directly involved in binding colicin E7. The selection may disproportionately favor these interface residues because they have been optimized by evolution to maximize the stability of the Im7-E7 complex, not the Im7 monomer. To get an idea of how much the function of Im7 had been affected by the stabilizing mutations, it was measured how well mutants in Im7 were able to inhibit the ability of exogenously added colicin E7 to kill a strain that expressed these mutants. The majority of the mutants were fully functional as measured by this assay. The residue that when mutated had the biggest effect on activity was N26 which shows two hydrogen bonds between Im7 and E7, both of these are modeled to be disrupted upon mutation of N26 to lysine.

Computational approaches have been used to predict the folding free energy of mutations in proteins (recently reviewed in protein folding handbook vol 2). The ability of two of these programs (PoPMuSiC and eris) to predict the stability of the Im7 mutants was tested. For the stabilizing single amino acid substitution mutations isolated, PoPMuSiC incorrectly predicted that 10/11 should be destabilizing. It performed significantly better with the previously isolated destabilizing mutations, correctly predicting that 5/6 should be destabilizing, although the value of the predicted change was different from the actual change. One possible reason for this superior ability to predict the destabilizing effect of mutants may be the fact that destabilizing mutants are much more common, which is reflected in the strongly biased training set used to develop popmusic.

Eris was much more successful in predicting that a mutant should have a stabilizing effect, correctly predicting that 12/13 of the single point mutations should be stabilizing, but eris overpredicted the magnitude of the stabilizing effect. Three of the 15 single substitutions obtained by antibiotic resistant selection, L18F, K20E, and V33E are commonly present in Im7 homologues. This is consistent with the consensus method for protein stabilization of Steipe et al. They suggest that consensus mutations, which replace a residue with the most common amino acid that is present in that position among family members, often lead to protein stabilization. This is a qualitative rather than quantitative prediction. Of the three consensus mutations isolated, only L18F increased the thermodynamic stability of Im7, and only by 0.8 kJ/mol. Both V33E and K20E decreased thermodynamic stability, and V33E decreased both thermodyamic stability and resulted in more rapid unfolding. In comparison to the three bioinformatics approaches tested, the experimental method is more accurate.

Example 2

Kanamycin Based Screening

Figure 6:
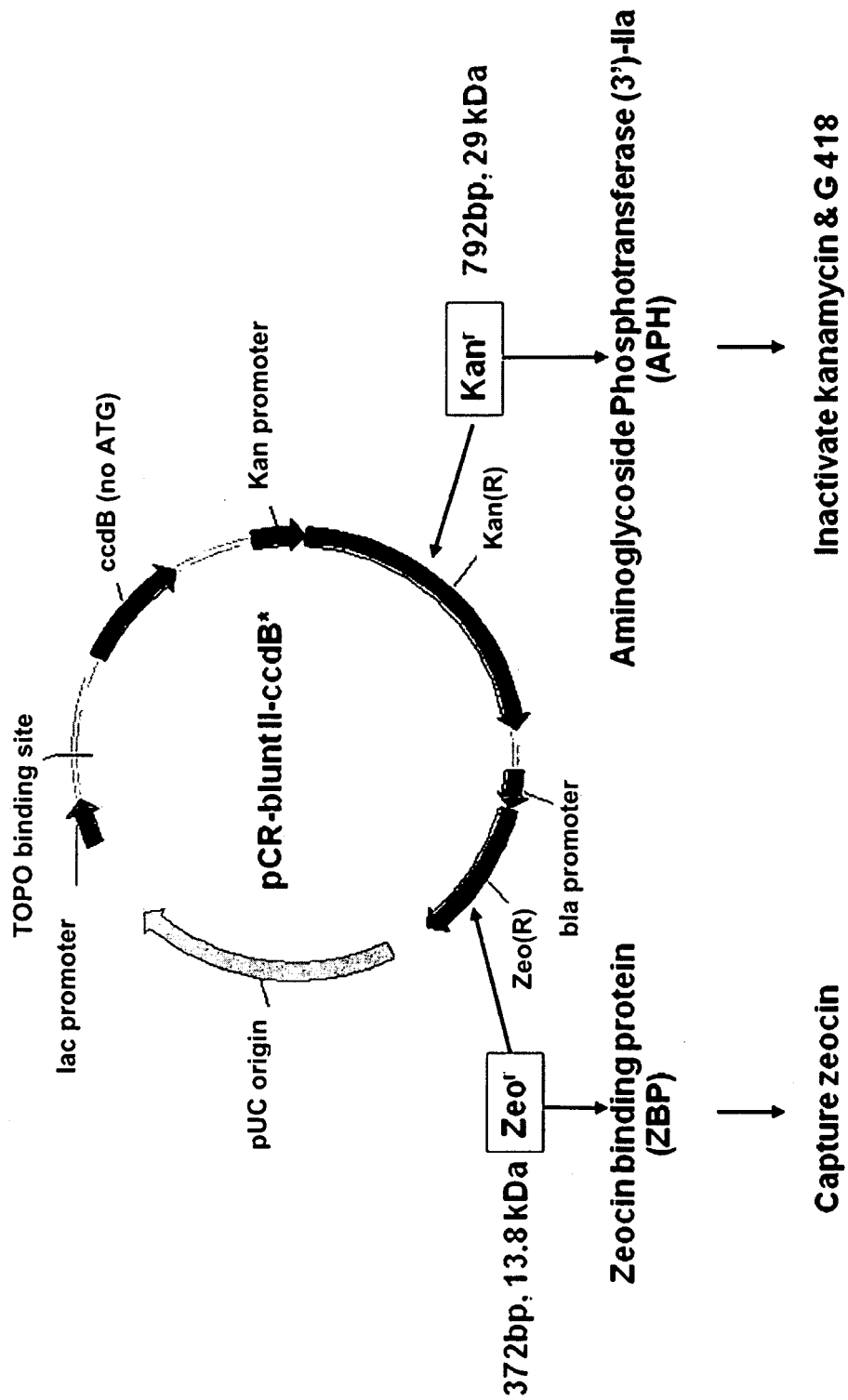
FIG. 6 shows selection markers for prokaryotes and eukaryotes.
Figure 8:
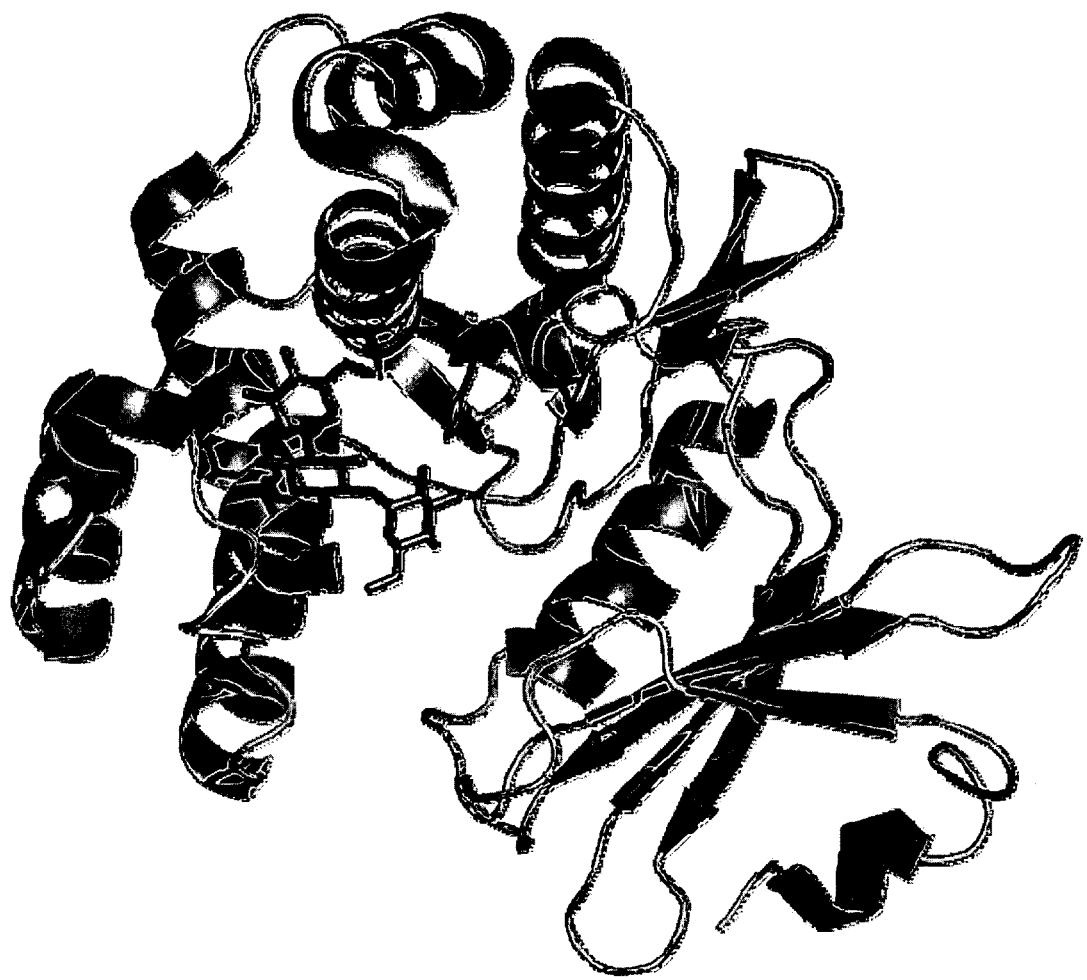
FIG. 8 shows the structure of APH(3')IIa.

This example describes the development of a cytosolic selection marker, useful in both eukaryotic and bacterial species, based upon tripartite fusion. Several antibiotics are active against a variety of prokaryotic and eukaryotic hosts. Aminoglycoside phosphotransferase (3')-IIa confers a selectable phenotype in both prokaryotic and eukaryotic cells. APH (3')-IIa is a 29 kDa two domain protein. The Kanamycin binding pocket is present on the conserved C domain (FIG. 8). APH (3')-IIa was present on high copy number plasmid pCR-blunt-II TOPO and expressed under its own promoter (FIG. 6). This plasmid was modified to inactivate the toxic ccdB gene by introducing a stop codon at position 5. Unique cleavage sites from pCR-blunt-II TOPO plasmid were removed by Nsi I digestion and relegation. The modified pCR-blunt-II TOPO vector was termed pTOPOccdB*.

Figure 7:
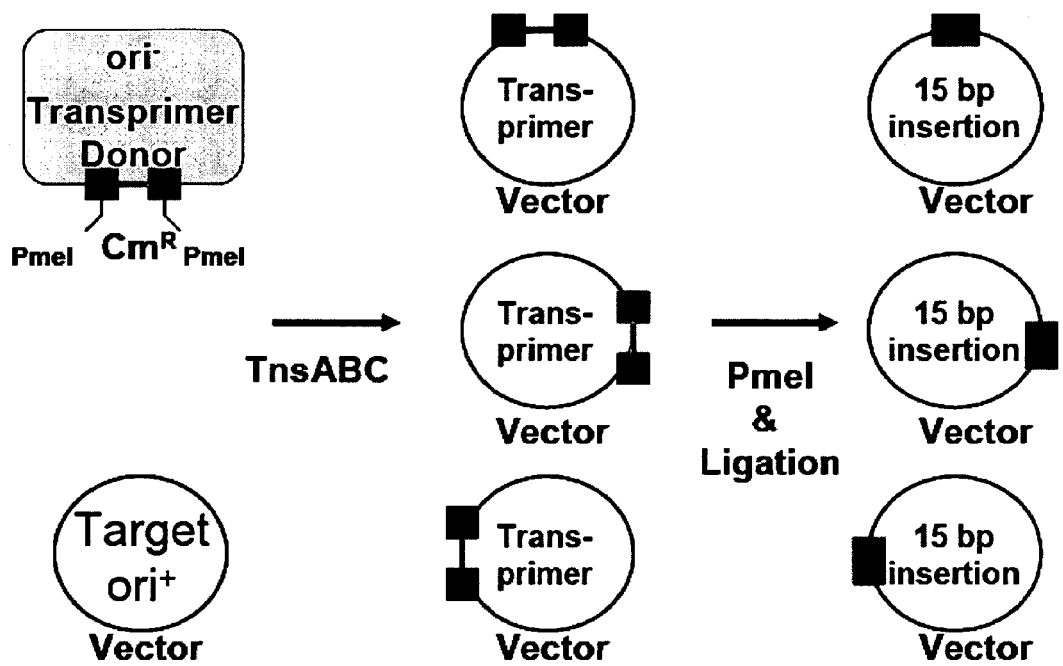
FIG. 7 shows GPS-LS linker scanning methods.

Insertion Site(s) in the APH (3')-IIa Protein were Determined Using the Tn7 GPS™-LS Linker scanning system from New England Biolabs. For in vitro transposition mutagenesis, Transprimer donor plasmid (ori-), termed Transprimer-4 donor, was used. In vitro transposon mutagenesis inserts a 1383 bp long DNA fragment (containing CmR and PmeI restriction sites at the ends) randomly into target plasmid pTOPOccdB* (FIG. 7). Insertion of transprimer-4 into APH(3')-IIa ORF or its promoter resulted in sensitivity towards kanamycin and gain of CmR. After transposition, 4000 KanS clones were collected. After 4 rounds of purification by replica plating on LBcm (34 µg/ml) and LBcm (34 µg/ml)+kan (100 µg/ml) plates, 1800 pure kanS clones were found. The APH(3')-IIa ORF has 264 codons. A library of 1800 KanS clones reflects nearly 6.8 times insertion at each codon. These kanS clones were grown in LBcm (34 µg/ml) liquid media. Equal volumes from each culture were pooled and plasmid was extracted. PmeI digestion of transposed pTOPOccdB* vector removed the majority of transposon (15 bp remains containing PmeI site). After relegation, the plasmid was transformed in NEB 10b cells and plated on LBkan (200 µg/ml) plates.

Figure 9:
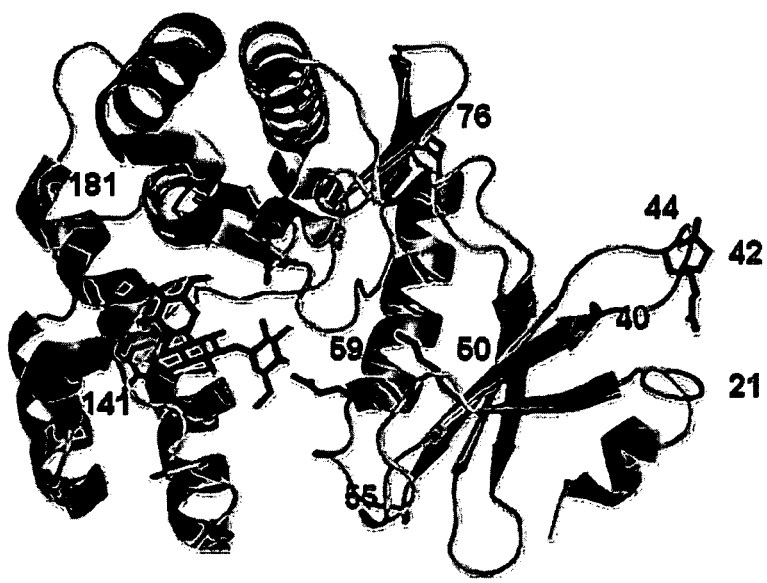
FIG. 9 shows penta-peptide insertion tolerance sites in the APH(3')IIa protein.

To locate insertion sites, clones were sequenced, which revealed insertions throughout APH(3')-IIa ORF. The majority of the insertion sites were in the N-domain of APH (FIG. 9). To find suitable immunity site for full length protein in the APH(3')-IIa, a destabilized variant of Im7 was used as model protein. Im7 F84A was amplified by primers 5' GGTT-TAAACGGTTCTGGTTCAGGCTCTGG-TAGCGGATCCGGCTCGAGCGGTTCCGG GAGCAGG-GAACTGAAAAATAGTATTAGTGATTAC 3' (SEQ ID NO:10) and 5' TCCGTTTAAACCAGAGCCACCCCCTC-CGCTTCCGGACCCTGAGGAGCCAGAGCTCG AAC-CGCCCTGTTTAGCTCCTGGCTTACCGTTAGC 3' (SEQ ID NO:11) to introduce 17 amino acid long Gly-Ser linker at both ends and unique octa-nucleotide (PmeI) recognition sites at both ends.

Figure 10:
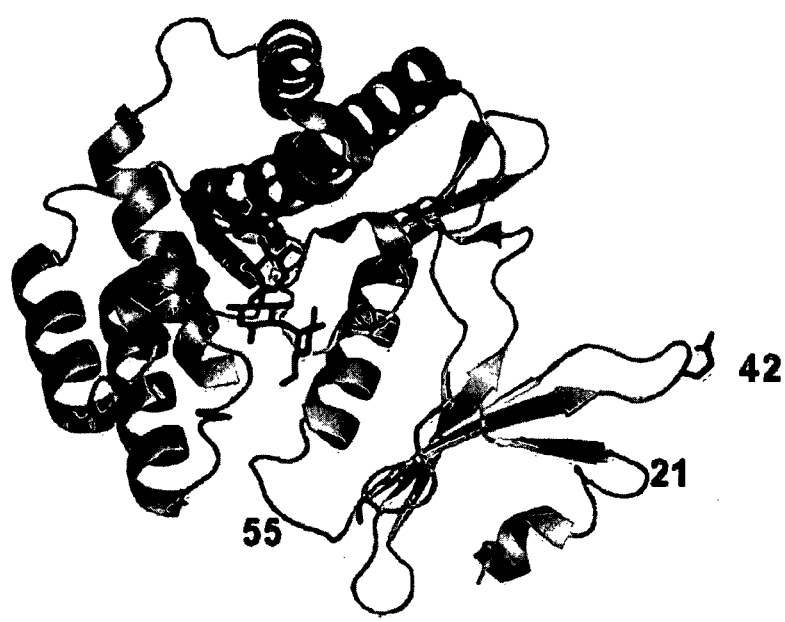
FIG. 10 shows protein insertion tolerance sites in the APH(3')IIa protein.

Im7 F84A was PCR amplified and sub-cloned into pCR-blunt-II TOPO. The sub-clone was sequenced and digested by PmeI. The Im7 F84A insert was agarose gel extracted, purified by QIAquick gel extraction kit (Qiagen), and quantified by agarose gel electrophoresis. The Im7 F84A insert was ligated into a PmeI digested and dephosphorylated library of 1800 kanS pTOPOccdB* vectors, transformed into NEB10b cells and plated onto LBkan (100 µg/ml). Sequencing of kanR clones revealed insertion of Im7 F84A at 4 different positions (11, 21, 42 and 55) in the APH(3')-IIa (FIG. 10). A Truncated (Δ2-10) version of APH-I (U.S. Pat. No. 5,116,750; herein incorporated by reference in its entirety) was active. The N-terminus of the whole APH family is non-conserved. The crystal structure of APH-II shows that this part is highly flexible. Therefore, position 11 was not considered for exploring as a potential tripartite insertion site. Im7 F84A inserted at position 21, 42 and 55 in The APH (3')-IIa was mutated to Im7 wt by site directed mutagenesis using primers

```
                                    (SEQ ID NO: 12)
5'CTAACGGTAAGCCAGGATTTAAACAGGGCTCCGGGA3'
And
                                    (SEQ ID NO: 13)
5'TCCCGGAGCCCTGTTTAAATCCTGGCTTACCGTTAG3'.
```

Figure 11:
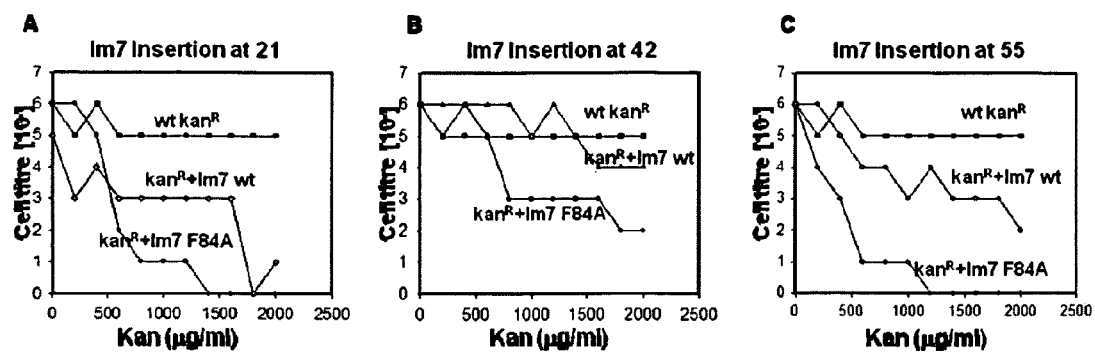
FIG. 11 shows MIC after lm7 (wt and F84A) insertion in APH(3')IIa protein.
Figure 12:
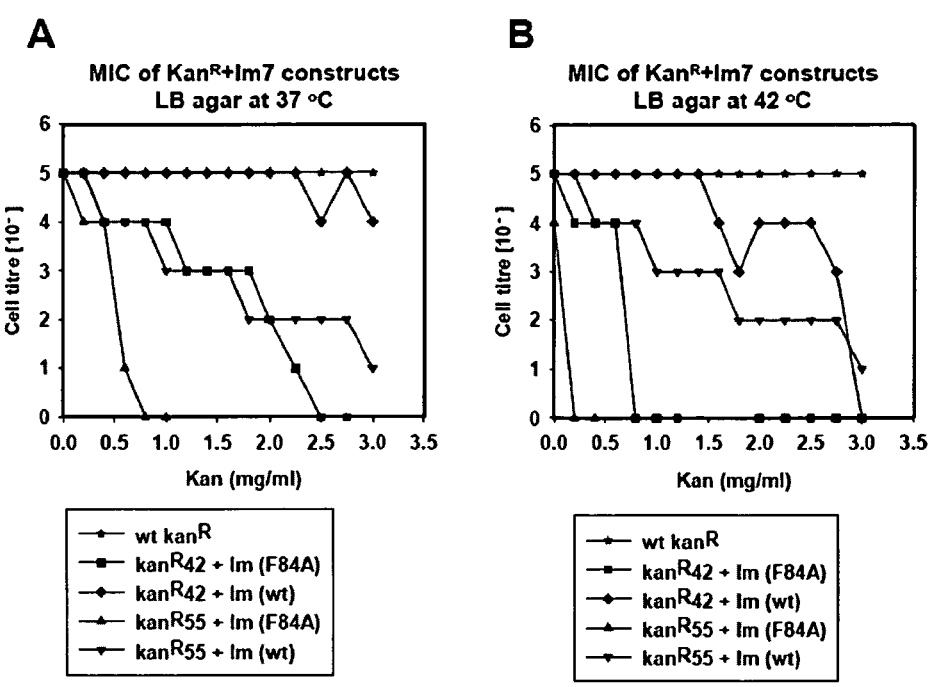
FIG. 12 shows the effects of LB medium on MIC of lm7 constructs.
Figure 13:
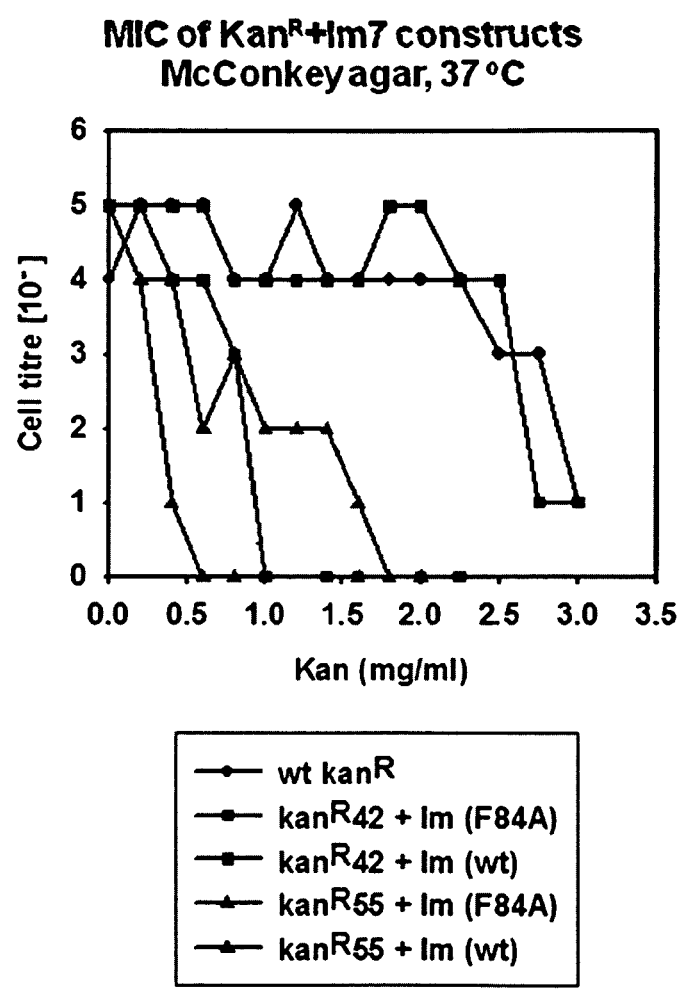
FIG. 13 shows the effects of McConkey broth on MIC of lm7 constructs.
Figure 14:
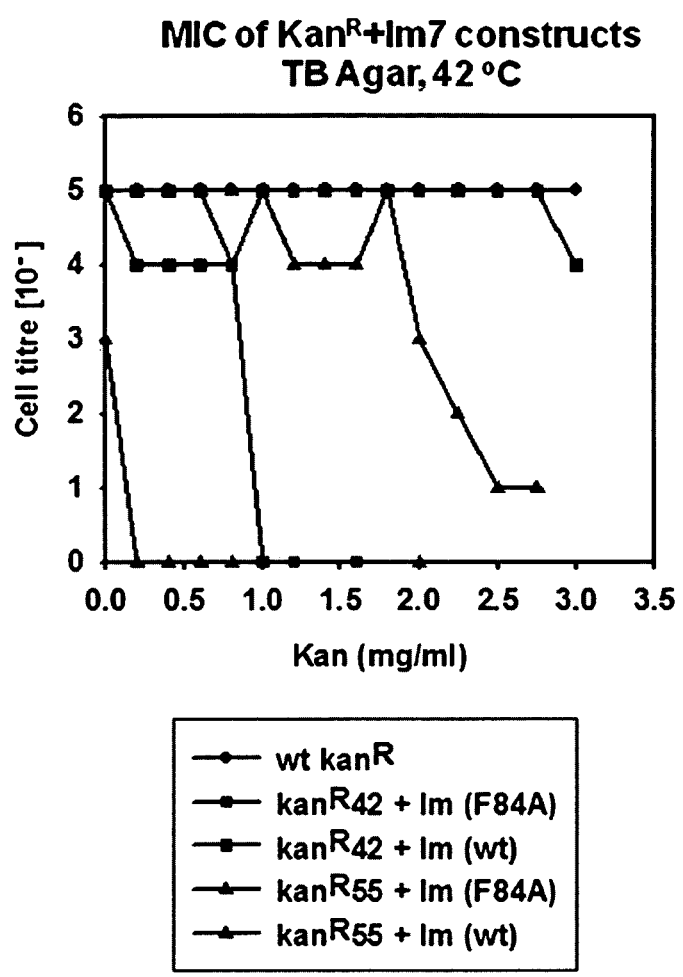
FIG. 14 shows the effects of Terrific broth on MIC of lm7 constructs.
Figure 15:
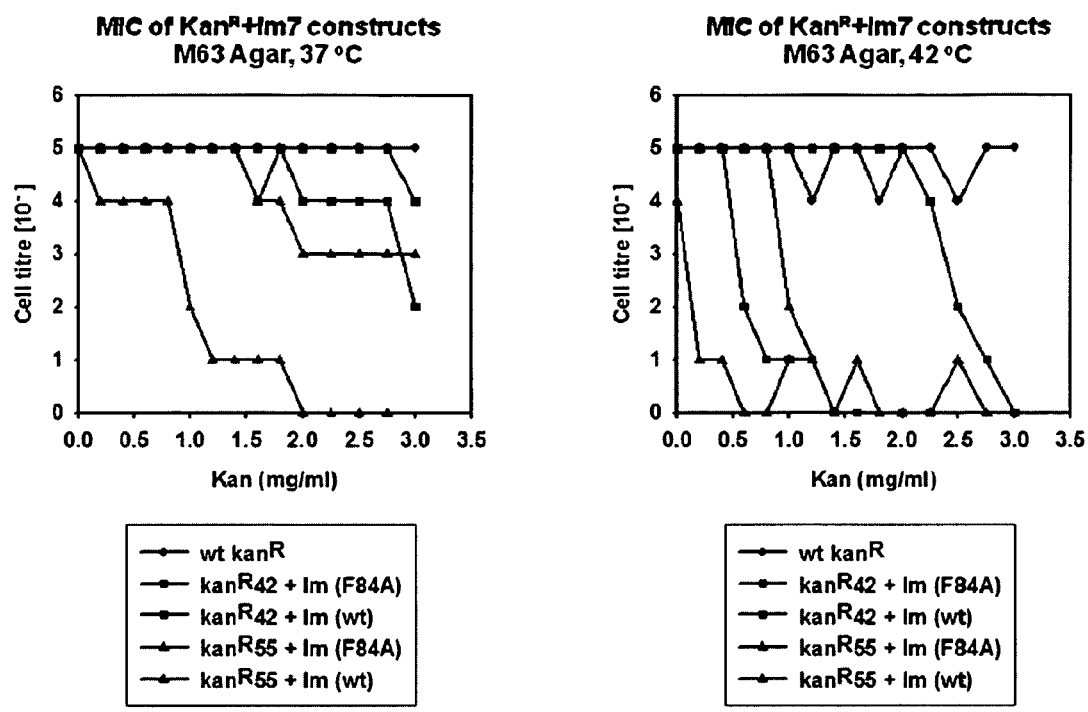
FIG. 15 shows the effects of M63 on MIC of lm7 constructs.

The preferred insertion immunity sites for a tripartite fusion were determined by evaluating minimal inhibitory concentrations of Im7 wt and Im7 F84A clones inserted at positions 21, 42 and 55 in the APH(3')-IIa (FIG. 11A-C) by spot titer methods. MIC of these constructs was evaluated using NEB10b strain in the LB media at 37° C. In all the cases, MIC differences were 2-3 logs. Truncated (2-50) APH (3')-IIa was inactive (Paschon D. E., Patel Z. S., and Ostermeier M (2005) JMB, 353, 26-37). Conserved residues are present at positions 30 and 32. Therefore, tripartite fusion constructs of Im7 (wt and F84A) at positions 42 and 55 in the APH(3')-IIa were used to optimize and obtain wide range of MICs between Kan-Im7 wt and kan-Im7 F84A. In the initial steps, cultivation parameters were optimized using NEB 10b cells. Growth conditions were optimized on five different medium (LB, McConkey, Terrific broth, M63 and Nutrient broth) and three different incubation temperatures (RT, 37 and 42° C.). At RT incubation, growth on LBkan plates was slow but MICs were higher than 37° C. incubation and differences between MICs of wt and F84A Im7 were low (1-2 logs). At 37° C., MICs were comparatively lower than RT incubation but differences in the MICs of wt-Im7 and F84A Im7 were up to 3-4 logs (FIG. 12A). At 42° C., MICs were further decreased and the log difference between wt-Im7 and Im7 F84A was 4-5 logs (FIG. 12B). MICs of Kan55-Im7 constructs were always lower than kan42-Im7 constructs. On the McConkey plates, MICs were lower than LB plates at all the temperature (FIG. 13). The MIC differences for Im7 wt and F84A at position 55 was 2 logs while at position 42 was 4 logs. Overall cells suffered on McConkey plates. On the TB plates, MICs of tripartite fusion constructs were higher than LB plates. At 42° C., there was nearly a 4 log difference between Kan55-Im7 wt and F84A while a 5 log difference was obtained for Kan42-Im7 wt and F84A (FIG. 14). The MIC on the M63 plates was overall similar to MICs on the LB plates. At 37° C., a 3 log difference was observed between Kan55-Im7 wt and F84A while at 42° C., nearly a 4 log difference was obtained between Kan55-Im7 wt and F84A and a 5 log difference was obtained between Kan42-Im7 wt and F84A (FIG. 15 A,B). In summary, the selection works well in a variety of media and temperatures.

Figure 16:
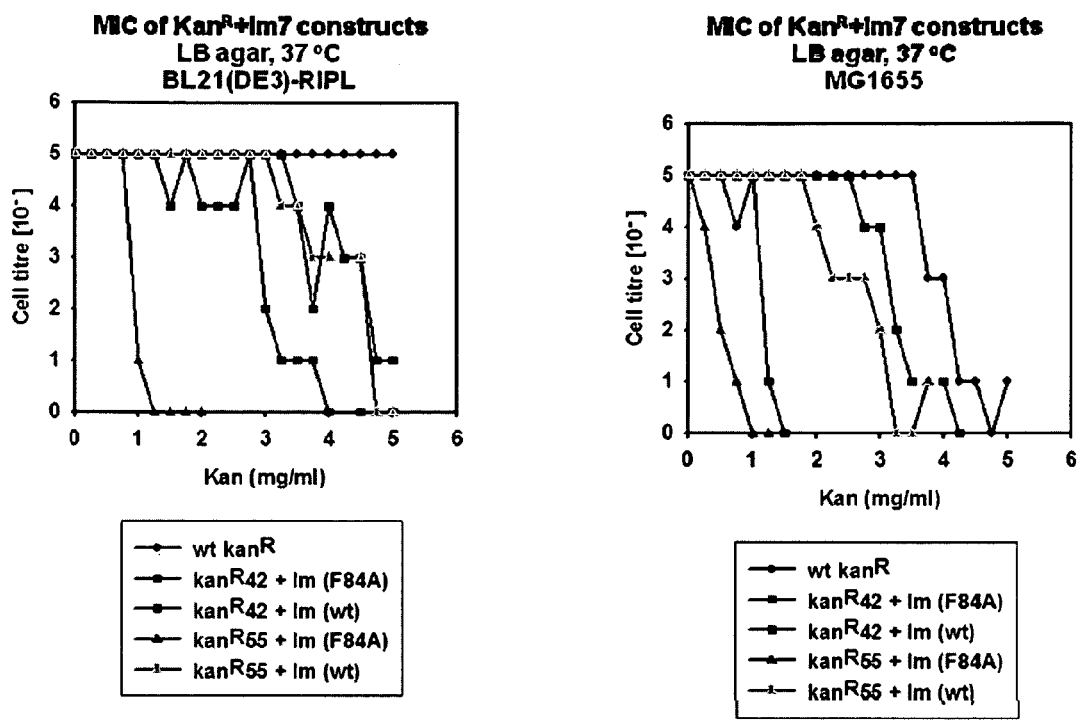
FIG. 16 shows the effects of strain E. coli on MIC of lm7 constructs.
Figure 17:
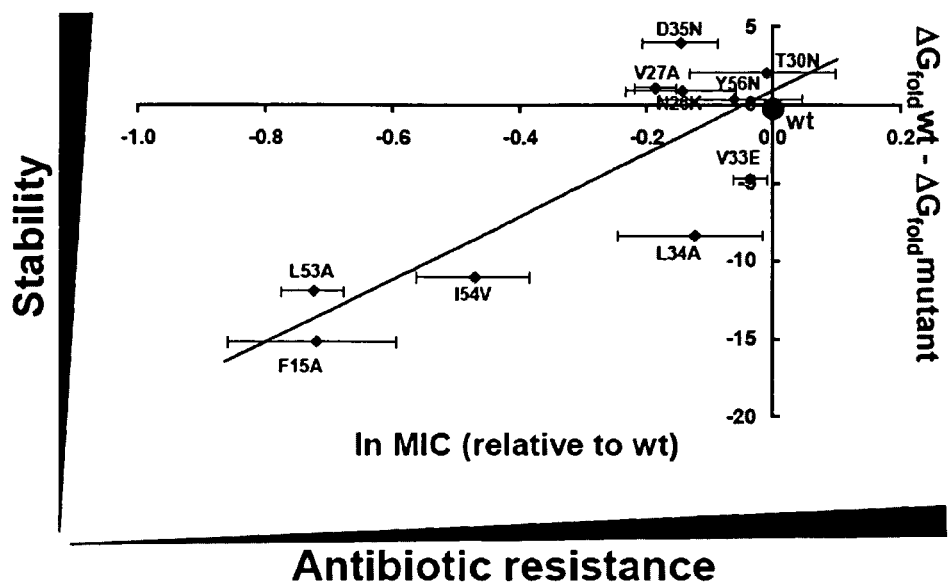
FIG. 17 shows a correlation between antibiotic resistance and stability for Im7 mutants in the kan screening system.

In the next step, BL 21(DE3)-RIPL (protease deficient strains) and MG1655 strains were evaluated in the LB media at 37° C. In the BL 21 strain, a 5 log difference for Kan55-Im7 wt and F84A was observed for nearly 2000 µg/ml kan while little discrimination for Im7 wt and F84A at kan42 was found (FIG. 16A). In the MG1655 strain, 5 log differences in the MICs of Kan55-Im7 wt and F84A and Kan42-Im7 wt and F84A were observed for nearly 1000 µg/ml kan (FIG. 16B). For further studies, position 55 in the APH(3')-IIa was utilized. BL21 was utilized as a host cell. Media and incubation temperature was LB and 37° C., respectively. These parameters were most suitable to discriminate MICs Kan55-Im7 wt and F84A up to 5 logs for a wide kanamycin concentration range (~2000 µg/ml) (FIG. 16A). Kan55-Im7 (wt) was mutated to several destabilized (F15A, L53A, I54V, L34A and V33E) and more stable variants (N26K, Y56N, V27A, T30N and D35N) than Im7 wt. It was observed that MIC of destabilized variants was dependent on their stabilities. Im7 variants having similar stability to wt Im7 showed indistinguishable MICs (FIG. 17).

Example 3

Zeocin Screening System

Figure 18:
FIG. 18 shows the structure of ZBP.

This example describes a selection system based upon resistance to Zeocin, which kills a wide range of prokaryotic and eukaryotic hosts. The ShBle gene confers resistance against Zeocin and is present on the high copy number pCR-blunt II-TOPO plasmid (FIG. 6) and expressed under control of a constitutive bla promoter. The ShBle gene (372 bp) encodes a 13.8 kDa protein which captures Zeocin (FIG. 18). To screen potential insertion sites in the ShBle, pCR-blunt II-TOPO was modified and subjected to transposan mutagenesis with transprimer-4 as mentioned in example 2. Transposition in the ShBle gene or its promoter resulted in the loss of Zeocin resistance and gain of CmR. After transposition and transformation in NEB10 b cells, 800 ZeocinS colonies were collected. These zeocinS colonies were purified by 4 rounds of replica plating, which resulted in 500 pure zeocinS clones. All the ZeocinS clones were pooled and plasmid was extracted. PmeI digestion removed the major part of the transposan cassette leaving 15 bp containing PmeI cleavage ends.

Figure 19:
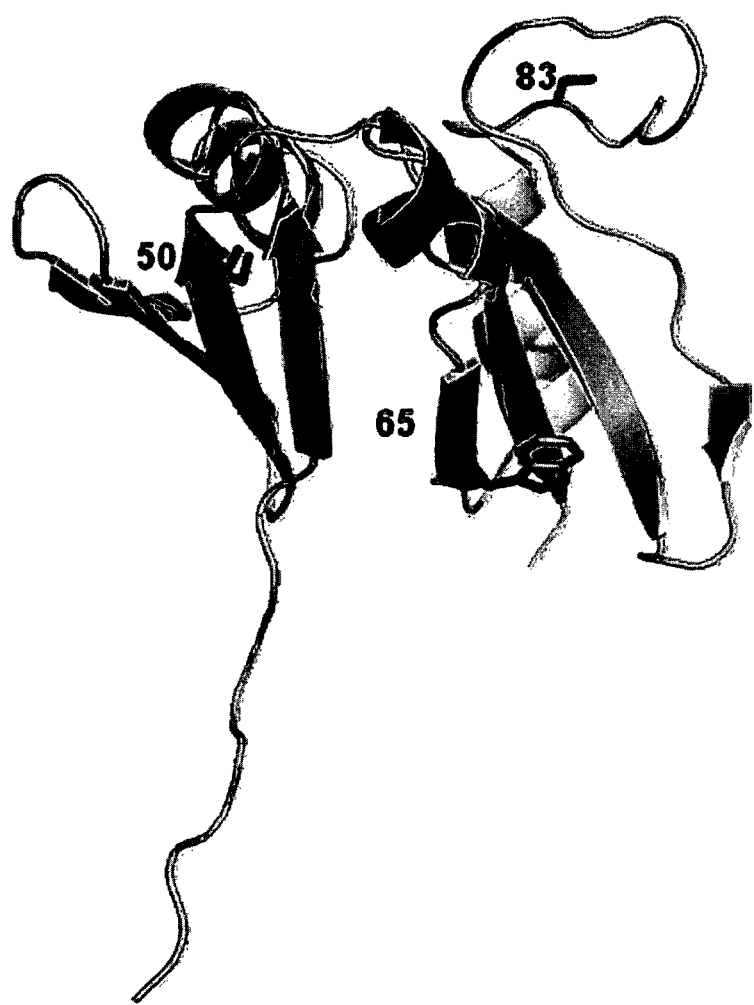
FIG. 19 shows protein insertion sites in ZBP.
Figure 20:
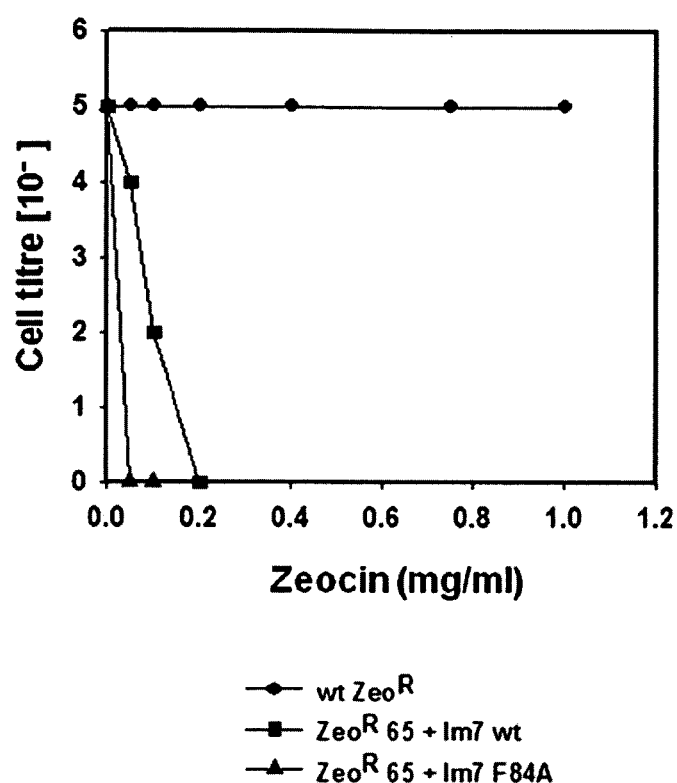
FIG. 20 shows MIC of Zeo65+lm7 wt and Zeo65+lm7 F84A.
Figure 21:
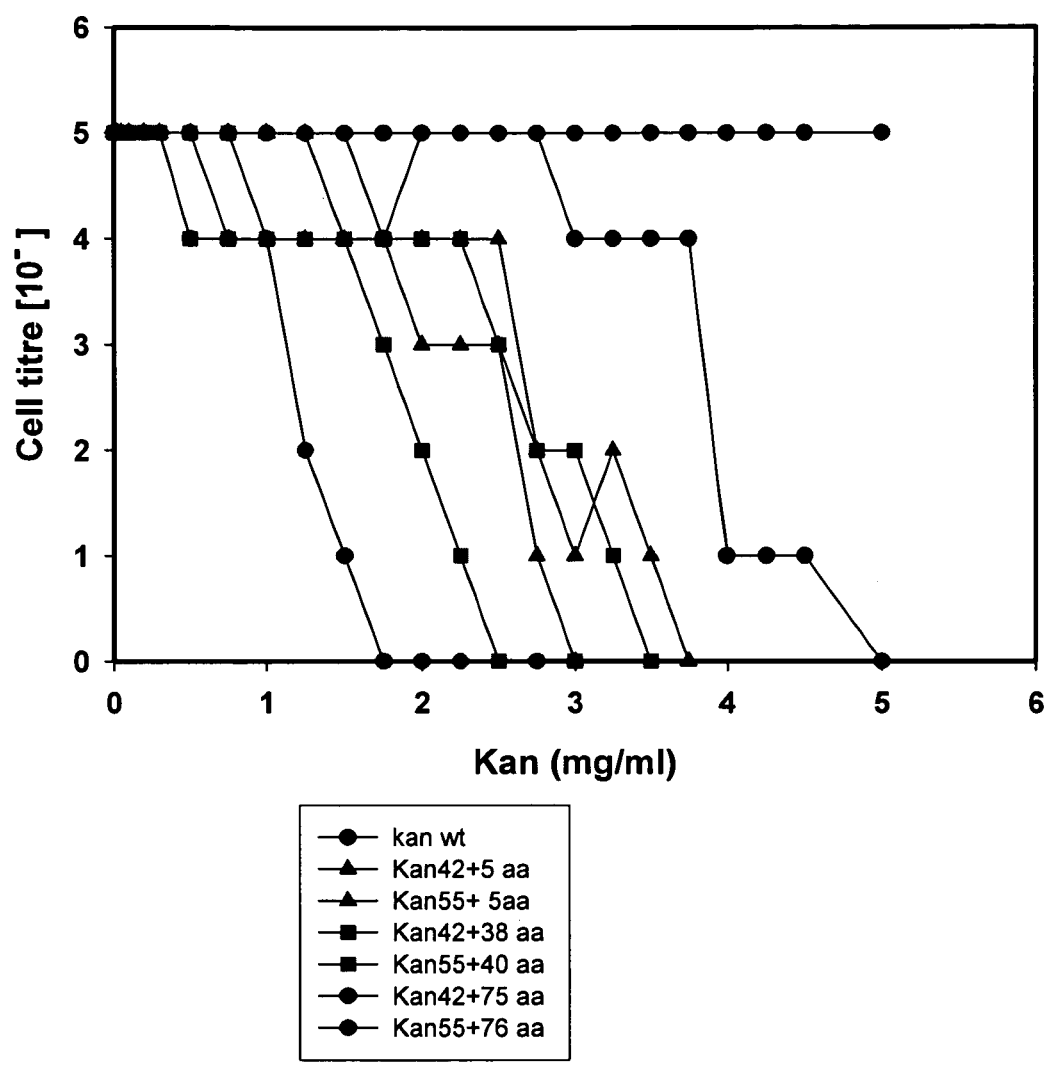
FIG. 21 shows the effect of linker length at position 42 and 55 of APH-(3')IIa.
Figure 22:
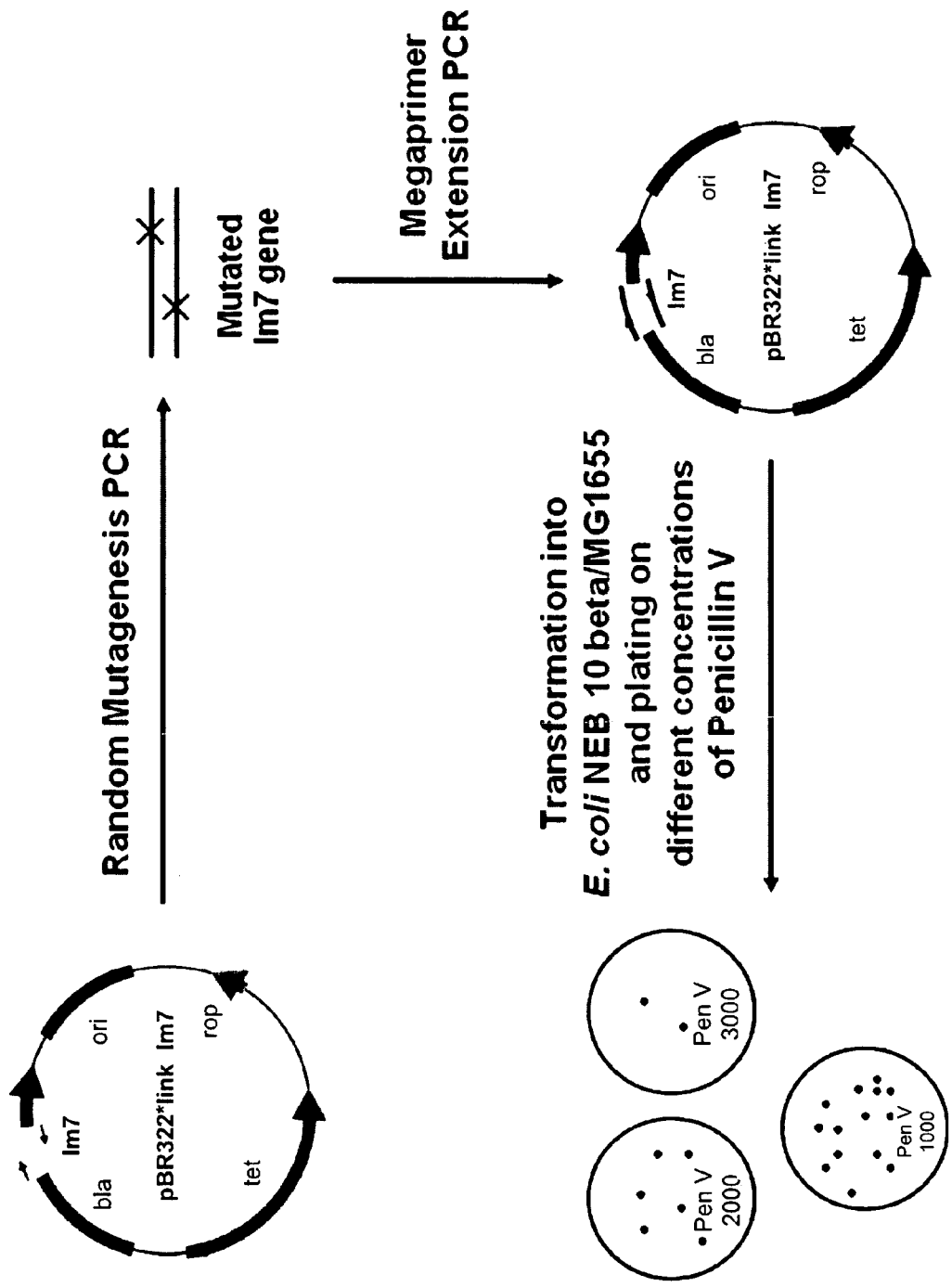
FIG. 22 shows an overview of mutagenesis and selection methods used in some embodiments of the present invention.
Figure 23:
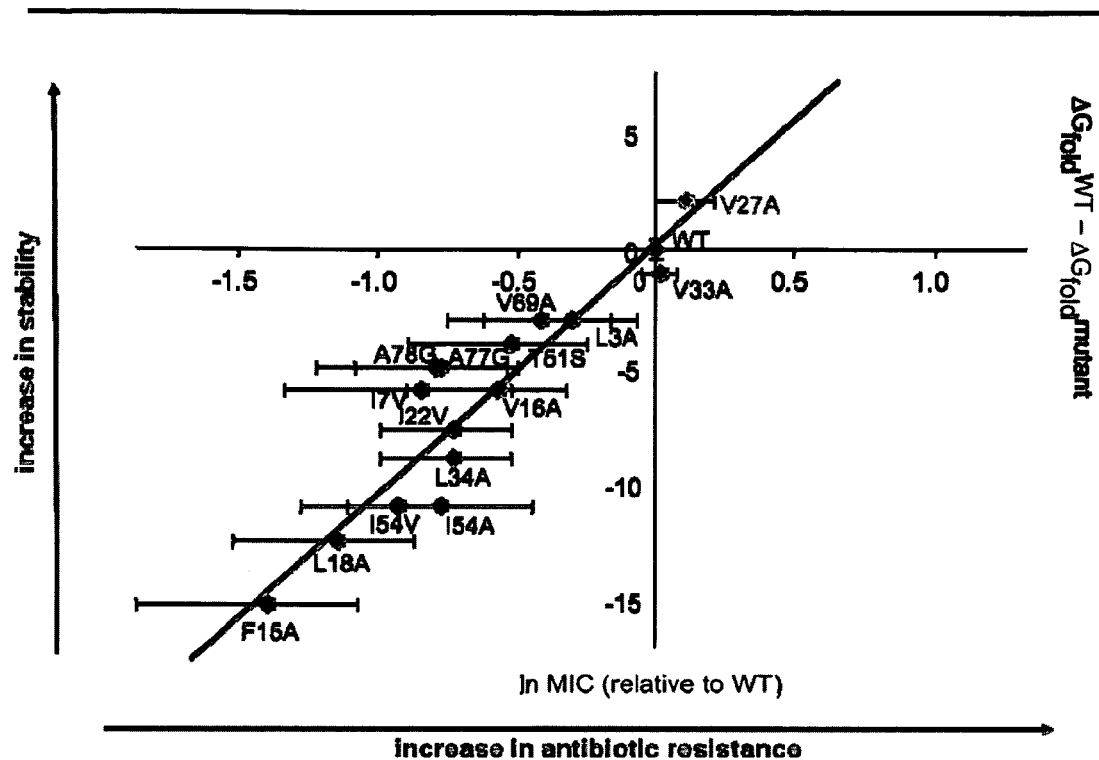
FIG. 23 shows a correlation between stability and antibiotic resistance for Im7 mutants in the β-lactamase screening system.
Figure 24:
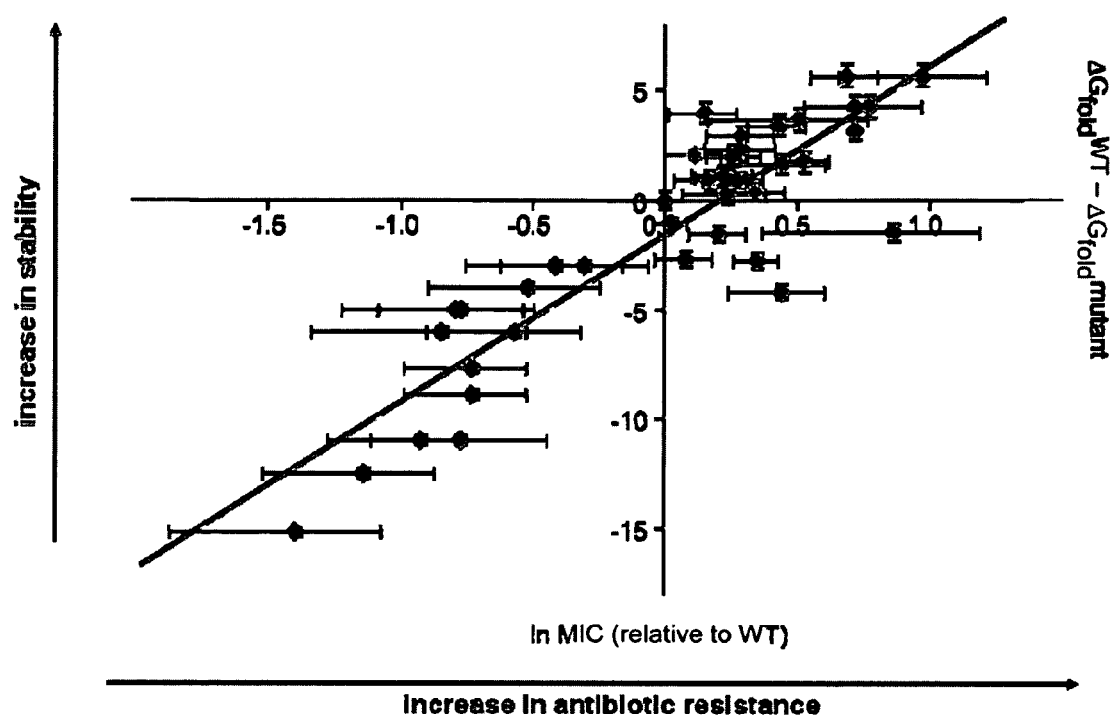
FIG. 24 shows Im7 mutants with increased antibiotic resistance.
Figure 26:
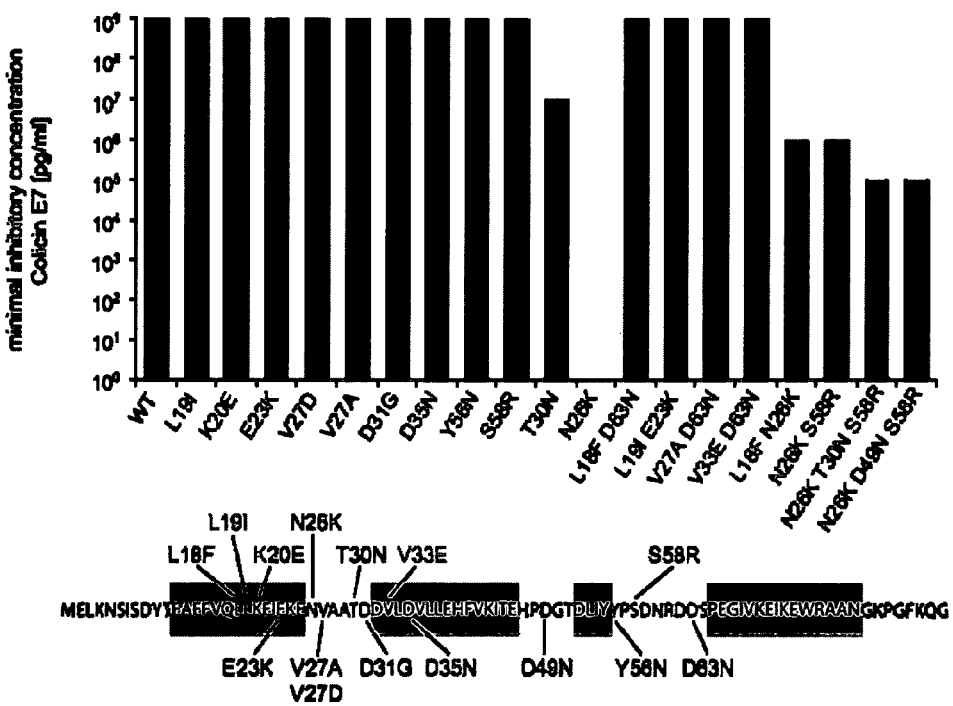
FIG. 26 shows the activity of Im7 mutants.
Figure 28:
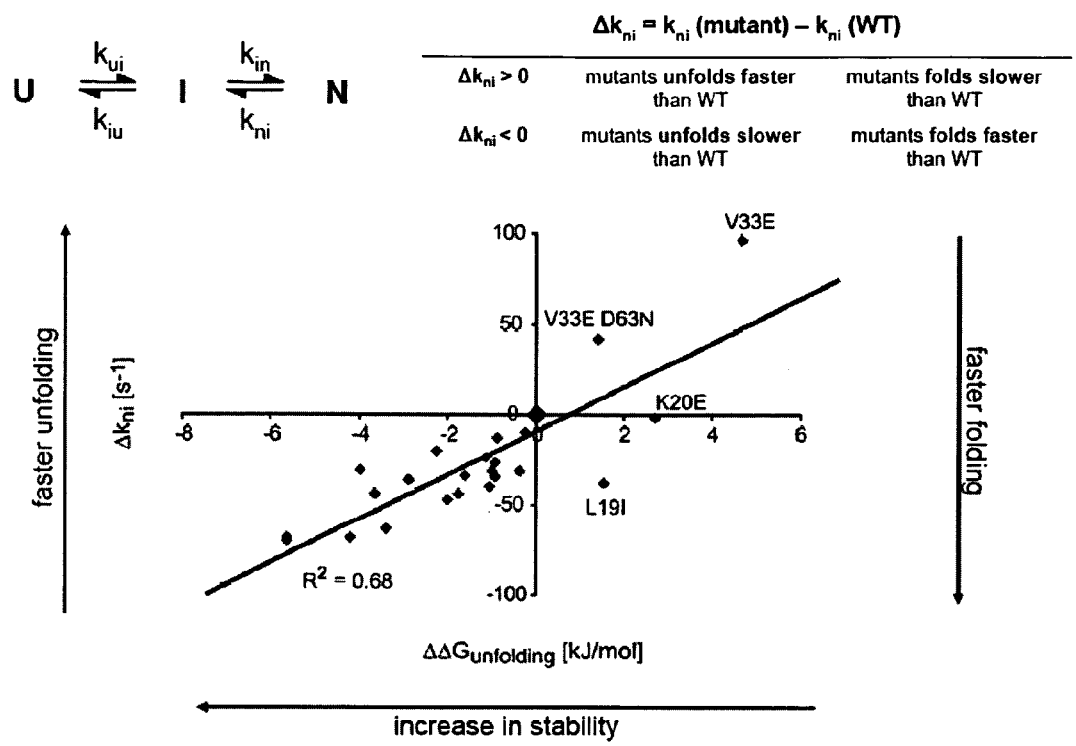
FIG. 28 shows the unfolding kinetics of Im7 mutants.
Figure 29:
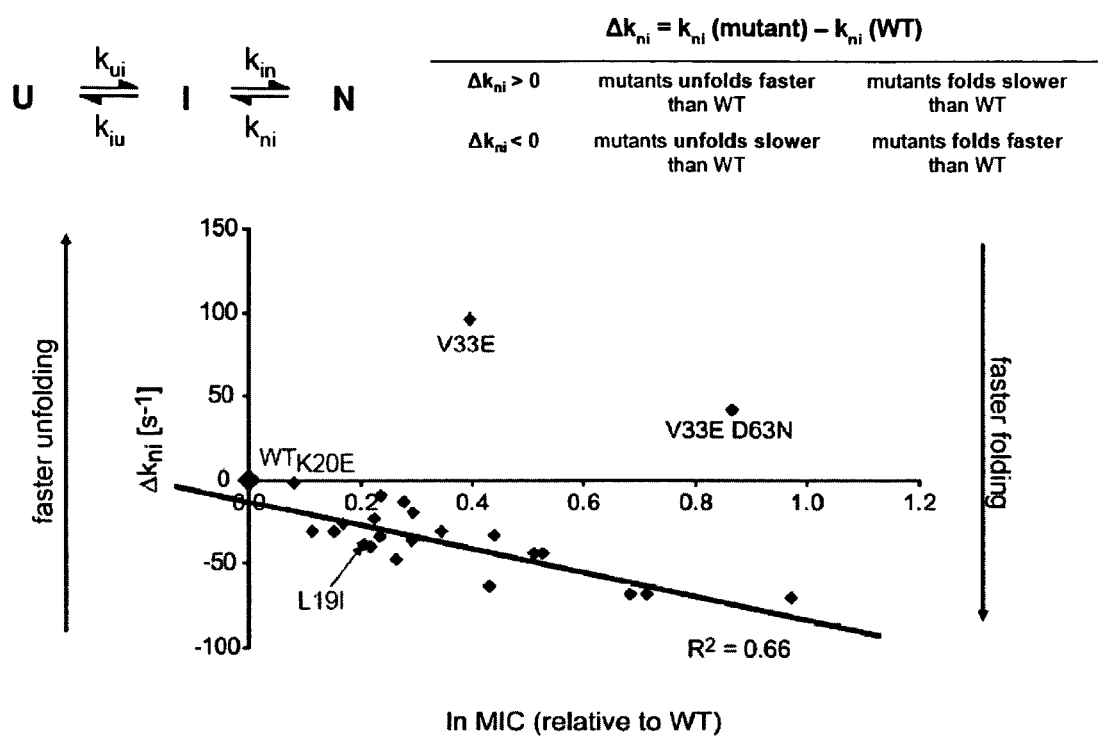
FIG. 29 shows the unfolding kinetics of Im7 mutants.
Figure 30:
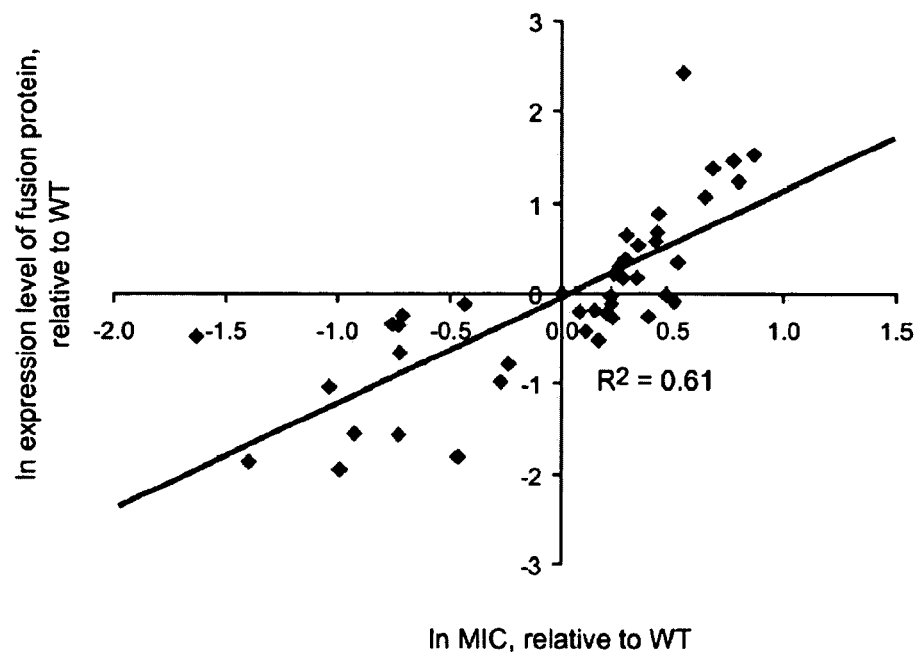
FIG. 30 shows expression levels of Im7 mutants.

To find insertion tolerable sites in the ZBP, Im7 wt flanked by 17 amino acid long Gly-Ser linker at both ends and PmeI restriction ends was ligated into a PmeI digested ZeoS library of pTOPOccdB*. Cells were transformed into NEB10b cells. Im7 wt was found at position 50, 65, 83 in the ZBP (FIG. 19). Im7 wt ligated at all the three positions was mutated to Im7 F84A by site directed mutagenesis. Potential immunity site in the ZBP were evaluated by MICs of ZBP50-Im7 (wt and F84A), ZBP65-Im7 (wt and F84A) and ZBP83-Im7 (wt and F84A). Position 65 in the ZBP discriminated MIC of ZBP tripartite fusion based upon stability of guest protein. Insertion of guest protein at position 65 decreases MIC severely (FIG. 20).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

---

The invention claimed is:

1. A method for identifying stable molecules of interest, comprising:
   a) Introducing mutations to one or more expression nucleic acids encoding molecules of interest;
   b) introducing one or more expression constructs encoding a fusion molecule into a plurality of said host cells, wherein said expression construct comprises a first gene encoding said molecules of interest inserted into a second gene that encodes a screenable marker;
   c) culturing said host cells in a cultured medium;
   d) exposing said plurality of host cells to a screening condition;
   e) assessing the stability of said molecules of interest by identifying cells that express a screenable marker, wherein expression of said screenable marker is the result of expression of stable molecules of interest;
   f) identifying stable molecules of interest by identifying host cells expressing stable molecules of interest, wherein said stable molecules of interest exhibit equal or increased expression of said screenable marker relative to the level of expression when wild type molecules of interest are inserted into said second gene; and
   g) isolating said host cells expressing said stable molecules of interest.

2. The method of claim 1, wherein said one or more expression constructs encode a plurality of mutants of said molecule of interest.

3. The method of claim 1, wherein said screenable marker is a selectable marker.

4. The method of claim 1, wherein said screening condition is a selection pressure.

5. The method of claim 1, further comprising the step of recombinantly producing said stable molecule of interest.

6. The method of claim 1, wherein said screenable marker is an antibiotic resistance gene.

7. The method of claim 6, wherein said antibiotic resistance gene is a β-lactamase gene.

8. The method of claim 6, wherein said antibiotic resistance gene is an aminoglycoside phosphotransferase (3')-IIa gene.

9. The method of claim 6, wherein said antibiotic resistance gene is a ShBle gene.

10. The method of claim 1, wherein molecule of interest is selected from the group consisting of a pharmaceutical protein, an industrial protein, a research protein, and an RNA.

11. The method of claim 1, wherein said one or more expression constructs encode a series of variants of said molecule of interest.

12. The method of claim 11, wherein said variants comprise amino acid changes.

13. The method of claim 11, wherein said variants result in altered disulfide bond formation in said molecule of interest.

14. The method of claim 11, wherein said variants result in altered hydrophobic interactions in said molecule of interest.

15. The method of claim 11, wherein said variants result in altered salt bridges in said molecule of interest.

16. The method of claim 11, wherein said culturing comprises exposing said host cells to a predefined screening condition, said predefined screening condition known to permit growth of host cells when said molecule of interest is a stable molecule and known to not permit growth of host cells when said molecule of interest is an unstable molecule.

17. The method of claim 11, wherein said host cell is prepared by the method comprising: exposing candidate host cells to a mutagen or mutagenic conditions to generate a population of mutated candidate host cells; expressing said expression construct in said population of mutated candidate host cells; applying a screening condition to said mutant candidate host cells such that a majority of said mutated candidate host cells do not grow; and selecting a mutant host cell that grows under said screening condition.

18. The method of claim 17, wherein said screening condition is a selective pressure.

* * * * *

UNITED STATES PATENT AND TRADEMARK OFFICE
CERTIFICATE OF CORRECTION

| | | |
|---|---|---|
| PATENT NO. | : 8,986,997 B2 | Page 1 of 1 |
| APPLICATION NO. | : 12/199060 | |
| DATED | : March 24, 2015 | |
| INVENTOR(S) | : James Bardwell et al. | |

It is certified that error appears in the above-identified patent and that said Letters Patent is hereby corrected as shown below:

IN THE CLAIMS:

Col. 38, lines 50 and 56.

CLAIM 16 reads: "The method of claim 11, wherein said culturing..."

CLAIM 17 reads: "The method of claim 11, wherein said host cell..."

HOWEVER, IT SHOULD READ:

CLAIM 16: "The method of claim 1, wherein said culturing..."

CLAIM 17: "The method of claim 1, wherein said host cell..."

Signed and Sealed this
Sixteenth Day of June, 2015

Michelle K. Lee
*Director of the United States Patent and Trademark Office*

SEQUENCE LISTING

<160> NUMBER OF SEQ ID NOS: 13

<210> SEQ ID NO 1
<211> LENGTH: 30
<212> TYPE: PRT
<213> ORGANISM: Artificial Sequence
<220> FEATURE:
<223> OTHER INFORMATION: Synthetic

<400> SEQUENCE: 1

Gly Gly Gly Gly Ser Gly Gly Gly Ser Ser Ser Gly Ser Gly Ser
1               5                   10                  15

Gly Ser Gly Ser Gly Gly Gly Gly Ser Gly Gly Gly Gly Ser
            20                  25                  30

<210> SEQ ID NO 2
<211> LENGTH: 87
<212> TYPE: DNA
<213> ORGANISM: Artificial Sequence
<220> FEATURE:
<223> OTHER INFORMATION: Synthetic

<400> SEQUENCE: 2
ccgctcccgg aacctgagga agaaccacca ccaccagaac caccaccacc tagttcgcca       60
gttaatagtt tgcgcaacgt tgttgcc                                          87

<210> SEQ ID NO 3
<211> LENGTH: 85
<212> TYPE: DNA
<213> ORGANISM: Artificial Sequence
<220> FEATURE:
<223> OTHER INFORMATION: Synthetic

<400> SEQUENCE: 3
aagtgggagc ggaggcggcg gatcaggcgg aggtggaagc ttgactctag ctagccggca       60
gcagctcata gactggatgg aggcg                                            85

<210> SEQ ID NO 4
<211> LENGTH: 34
<212> TYPE: DNA
<213> ORGANISM: Artificial Sequence
<220> FEATURE:
<223> OTHER INFORMATION: Synthetic

<400> SEQUENCE: 4
gttccggaag cggaggaggt ggttcaggcg gagg                                  34

<210> SEQ ID NO 5
<211> LENGTH: 30
<212> TYPE: DNA

```
<213> ORGANISM: Artificial Sequence
<220> FEATURE:
<223> OTHER INFORMATION: Synthetic

<400> SEQUENCE: 5
cgctcccgga tcctgagctc gagccaccac                                    30

<210> SEQ ID NO 6
<211> LENGTH: 90
<212> TYPE: DNA
<213> ORGANISM: Artificial Sequence
<220> FEATURE:
<223> OTHER INFORMATION: Synthetic

<400> SEQUENCE: 6
cgggagcggg agctcttctg gttccggagg cggtggagga tcaggcggtg gcggatcagg    60
aagtgggagc ggaggcggcg gatcaggcgg                                    90

<210> SEQ ID NO 7
<211> LENGTH: 86
<212> TYPE: DNA
<213> ORGANISM: Artificial Sequence
<220> FEATURE:
<223> OTHER INFORMATION: Synthetic

<400> SEQUENCE: 7
gaactcgagc caccggatcc tgagccacca ccaccagatc cccgccacc tgaacctgag     60 gaagaaccac caccaccaga accacc                                        86

<210> SEQ ID NO 8
<211> LENGTH: 25
<212> TYPE: DNA
<213> ORGANISM: Artificial Sequence
<220> FEATURE:
<223> OTHER INFORMATION: Synthetic

<400> SEQUENCE: 8
atggaactga aaatagtat tagtg                                          25

<210> SEQ ID NO 9
<211> LENGTH: 18
<212> TYPE: DNA
<213> ORGANISM: Artificial Sequence
<220> FEATURE:
<223> OTHER INFORMATION: Synthetic

<400> SEQUENCE: 9
gccctgttta aatcctgg                                                 18

<210> SEQ ID NO 10
<211> LENGTH: 90
<212> TYPE: DNA
<213> ORGANISM: Artificial Sequence
<220> FEATURE:
<223> OTHER INFORMATION: Synthetic

<400> SEQUENCE: 10
ggtttaaacg gttctggttc aggctctggt agcggatccg gctcgagcgg ttccgggagc    60
agggaactga aaatagtat tagtgattac                                     90

<210> SEQ ID NO 11
<211> LENGTH: 90
<212> TYPE: DNA
<213> ORGANISM: Artificial Sequence
```

```
<220> FEATURE:
<223> OTHER INFORMATION: Synthetic

<400> SEQUENCE: 11
tccgtttaaa ccagagccac cccctccgct tccggaccct gaggagccag agctcgaacc      60
gccctgttta gctcctggct taccgttagc                                       90

<210> SEQ ID NO 12
<211> LENGTH: 36
<212> TYPE: DNA
<213> ORGANISM: Artificial Sequence
<220> FEATURE:
<223> OTHER INFORMATION: Synthetic

<400> SEQUENCE: 12
ctaacggtaa gccaggattt aaacagggct ccggga                                36

<210> SEQ ID NO 13
<211> LENGTH: 36
<212> TYPE: DNA
<213> ORGANISM: Artificial Sequence
<220> FEATURE:
<223> OTHER INFORMATION: Synthetic

<400> SEQUENCE: 13
tcccggagcc ctgtttaaat cctggcttac cgttag                                36
```